United States Patent
DeBenedictis et al.

(10) Patent No.: US 10,806,500 B2
(45) Date of Patent: Oct. 20, 2020

(54) TREATMENT SYSTEMS, METHODS, AND APPARATUSES FOR IMPROVING THE APPEARANCE OF SKIN AND PROVIDING OTHER TREATMENTS

(71) Applicant: Zeltiq Aesthetics, Inc., Pleasanton, CA (US)

(72) Inventors: Leonard C. DeBenedictis, Dublin, CA (US); George Frangineas, Jr., Fremont, CA (US); Kristine Tatsutani, Redwood City, CA (US); Linda Pham, Kensington, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 0 days.

(21) Appl. No.: 16/233,951

(22) Filed: Dec. 27, 2018

(65) Prior Publication Data

US 2019/0125424 A1    May 2, 2019

Related U.S. Application Data

(62) Division of application No. 14/611,127, filed on Jan. 30, 2015, now Pat. No. 10,201,380.

(Continued)

(51) Int. Cl.
*A61B 18/02*    (2006.01)
*A61F 7/00*    (2006.01)
(Continued)

(52) U.S. Cl.
CPC ......... *A61B 18/02* (2013.01); *A61B 18/0206* (2013.01); *A61B 90/04* (2016.02);
(Continued)

(58) Field of Classification Search
CPC ............ A61B 18/02; A61B 2018/0237; A61B 2018/0243; A61B 2018/025;
(Continued)

(56) References Cited

U.S. PATENT DOCUMENTS

| 681,806 A | 9/1901 | Mignault et al. |
| 889,810 A | 6/1908 | Robinson et al. |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.

(Continued)

*Primary Examiner* — Thomas A Giuliani
(74) *Attorney, Agent, or Firm* — Perkins Coie LLP

(57) ABSTRACT

Treatment systems, methods, and apparatuses for improving the appearance of skin or other target regions are described as well as for providing for other treatments. Aspects of the technology are directed to improving the appearance of skin by tightening the skin, improving skin tone or texture, eliminating or reducing wrinkles, increasing skin smoothness, or improving the appearance of cellulite. Treatments can include cooling a surface of a patient's skin and detecting at least one freeze event in the cooled skin. The treatment system can continue cooling the patient's skin after the freeze event(s) are detected so to maintain at least a partially frozen state of the tissue for a period of time.

13 Claims, 10 Drawing Sheets

Related U.S. Application Data

(60) Provisional application No. 61/934,549, filed on Jan. 31, 2014, provisional application No. 61/943,250, filed on Feb. 21, 2014, provisional application No. 61/943,257, filed on Feb. 21, 2014.

(51) Int. Cl.
*A61H 1/00* (2006.01)
*A61N 7/00* (2006.01)
*A61K 31/045* (2006.01)
*A61K 31/047* (2006.01)
*A61B 90/00* (2016.01)
*A61B 18/00* (2006.01)

(52) U.S. Cl.
CPC ............... *A61F 7/00* (2013.01); *A61F 7/007* (2013.01); *A61H 1/006* (2013.01); *A61H 1/008* (2013.01); *A61K 31/045* (2013.01); *A61K 31/047* (2013.01); *A61N 7/00* (2013.01); *A61B 2018/00291* (2013.01); *A61B 2018/00464* (2013.01); *A61B 2018/00714* (2013.01); *A61B 2018/00791* (2013.01); *A61B 2018/00875* (2013.01); *A61B 2018/00994* (2013.01); *A61B 2018/0237* (2013.01); *A61B 2018/0262* (2013.01); *A61B 2090/0463* (2016.02); *A61B 2090/065* (2016.02); *A61F 2007/0003* (2013.01); *A61F 2007/0004* (2013.01); *A61F 2007/0019* (2013.01); *A61F 2007/0036* (2013.01); *A61F 2007/0045* (2013.01); *A61F 2007/0047* (2013.01); *A61F 2007/0052* (2013.01); *A61F 2007/0056* (2013.01); *A61F 2007/0075* (2013.01); *A61F 2007/0087* (2013.01); *A61F 2007/0093* (2013.01); *A61F 2007/0096* (2013.01)

(58) Field of Classification Search
CPC .... A61B 2018/0256; A61B 2018/0262; A61B 2018/00452; A61B 2018/00458; A61B 2018/00464; A61B 90/04; A61B 2090/0463; A61F 2007/0052; A61F 2007/0056; A61F 2007/0075; A61F 2007/029
USPC ......... 606/20, 22–26; 607/96, 104, 107–109, 607/114
See application file for complete search history.

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,341,230 A | 9/1967 | Wichers |
| 3,502,080 A | 3/1970 | Hirschhorn |
| 3,566,871 A | 3/1971 | Richter et al. |
| 3,587,577 A | 6/1971 | Zubkov et al. |
| 3,591,645 A | 7/1971 | Selwitz |
| 3,692,338 A | 9/1972 | Didier |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |

(56) References Cited

U.S. PATENT DOCUMENTS

| | | |
|---|---|---|
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |

(56) References Cited

U.S. PATENT DOCUMENTS

| | | |
|---|---|---|
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| D568,258 S | 5/2008 | Adam |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,676,338 B2 | 3/2014 | Levinson |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 8,840,608 B2 | 9/2014 | Anderson et al. |
| 9,132,031 B2 | 9/2015 | Levinson et al. |
| 9,149,322 B2 | 10/2015 | Knowlton |
| 9,308,120 B2 | 4/2016 | Anderson et al. |
| 9,314,368 B2 | 4/2016 | Allison et al. |
| 9,358,149 B2 | 6/2016 | Anderson et al. |
| 9,375,345 B2 | 6/2016 | Levinson et al. |
| 9,408,745 B2 | 8/2016 | Levinson et al. |
| D777,338 S | 1/2017 | Coakley |
| 9,545,523 B2 | 1/2017 | Nanda |
| 9,649,220 B2 | 5/2017 | Anderson et al. |
| 9,655,770 B2 | 5/2017 | Levinson et al. |
| 9,737,434 B2 | 8/2017 | Allison |
| 9,844,460 B2 | 12/2017 | Weber et al. |
| 9,844,461 B2 | 12/2017 | Levinson et al. |
| 9,861,421 B2 | 1/2018 | O'Neil et al. |
| 9,861,520 B2 | 1/2018 | Baker et al. |
| 10,092,346 B2 | 10/2018 | Levinson |
| 10,201,380 B2 | 2/2019 | DeBenedictis et al. |
| 10,292,859 B2 | 5/2019 | Levinson et al. |
| 10,383,787 B2 | 8/2019 | Rosen et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |

(56) References Cited

U.S. PATENT DOCUMENTS

| | | |
|---|---|---|
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0281789 A1 | 12/2005 | Rao et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |

(56) References Cited

U.S. PATENT DOCUMENTS

| | | |
|---|---|---|
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1* | 1/2012 | Levinson ............... A61B 18/02 606/33 |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0303104 A1 | 11/2012 | Levy |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0185440 A1 | 7/2013 | Blau et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1* | 10/2014 | Anderson ............... A61B 18/02 607/104 |
| 2015/0112412 A1 | 4/2015 | Anderson et al. |
| 2015/0209174 A1 | 7/2015 | Abreu |
| 2015/0216719 A1 | 8/2015 | Debenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0089550 A1 | 3/2016 | DeBenedictis et al. |
| 2016/0135985 A1 | 5/2016 | Anderson |
| 2016/0317346 A1 | 11/2016 | Kovach |
| 2016/0324684 A1 | 11/2016 | Levinson et al. |
| 2017/0007309 A1* | 1/2017 | DeBenedictis ......... A61F 7/007 |
| 2017/0079833 A1 | 3/2017 | Frangineas, Jr. et al. |

(56) References Cited

U.S. PATENT DOCUMENTS

| | | |
|---|---|---|
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0319378 A1 | 11/2017 | Anderson et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0161197 A1 | 6/2018 | Baker et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0000663 A1 | 1/2019 | Anderson et al. |
| 2019/0125424 A1 | 5/2019 | DeBenedictis et al. |
| 2019/0142493 A1 | 5/2019 | Debenedictis et al. |
| 2019/0224042 A1 | 7/2019 | Ting et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| EP | 2904986 A1 | 8/2015 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |

(56) References Cited

FOREIGN PATENT DOCUMENTS

| | | |
|---|---|---|
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (*Cold panniculitis*)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.

Heller Page, E. et al., "Temperature-dependent skin disorders," Journal of the American Academy of Dermatology, vol. 18, No. 5, Pt 1, May 1988, pp. 1003-1019.

Hemmingsson, A. et al. "Attenuation in Human Muscle and Fat Tissue in Vivo and in Vitro," Acra Radiologica Diagnosis, vol. 23, No. 2, 1982, pp. 149-151.

Henry, F. et al., "Les Dermatoses Hivernales," Rev Med Liege, 54:11, 1999, pp. 864-866. [Abstract Attached].

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Holland, DB. et al. "Cold shock induces the synthesis of stress proteins in human keratinocytes," PubMed Journal of Investigative Dermatology; 101(2): Aug. 1993, pp. 196-199.

Holman, W. L. et al., "Variation in Cryolesion Penetration Due to Probe Size and Tissue Thermal Conductivity," The Annals of Thoracic Surgery, vol. 53, 1992, pp. 123-126.

Hong, J.S. et al., "Patterns of Ice Formation in Normal and Malignant Breast Tissue," Cryobiology 31, 1994, pp. 109-120.

Huang et al. "Comparative Proteomic Profiling of Murine Skin," Journal of Investigative Dermatology, vol. 121(1), Jul. 2003, pp. 51-64.

International Search Report and Written Opinion dated May 8, 2015; International Patent Application No. PCT/US2015/013985; 8 pages.

Isambert, H. "Understanding the Electroporation of Cells and Artificial Bilayer Membranes," Physical Review Letters, vol. 80, No. 15, 1998, pp. 3404-3707.

Jalian, H. R. et al., "Cryolipolysis: A Historical Perspective and Current Clinical Practice", 32(1) Semin. Cutan. Med. Surg., 2013, pp. 31-34.

Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.

(56) References Cited

OTHER PUBLICATIONS

Koska, J. et al., "Endocrine Regulation of Subcutaneous Fat Metabolism During Cold Exposure in Humans," Annals of the New York Academy of Sciences, vol. 967, 2002, pp. 500-505.

Kundu, S. K. et al., "Breath Acetone Analyzer: Diagnostic Tool to Monitor Dietary Fat Loss," Clinical Chemistry, vol. 39, Issue (1), 1993, pp. 87-92.

Kundu, S. K. et al., "Novel Solid-Phase Assay of Ketone Bodies in Urine," Clinical Chemistry, vol. 37, Issue (9), 1991, pp. 1565-1569.

Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.

Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.

Levchenko et al., "Effect of Dehydration on Lipid Metabolism" Ukrainskii Biokhimicheskii Zhurnal, vol. 50, Issue 1, 1978, pp. 95-97.

Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.

Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.

L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.

Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.

Manstein, D. et al. "A Novel Cryotherapy Method of Non-invasive, Selective Lipolysis," LasersSurg.Med 40:S20, 2008, p. 104.

Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.

Mayoral, "Case Reports: Skin Tightening with a Combined Unipolar and Bipolar Radiofrequency Device," Journal of Drugs in Dermatology, 2007, pp. 212-215.

Mazur, P. "Cryobiology: The Freezing of Biological Systems," Science, 68, 1970, pp. 939-949.

Merrill, T. "A Chill to the Heart: A System to Deliver Local Hypothermia Could One Day Improve the Lives of Heart-Attack Patients," Mechanical Engineering Magazine, Oct. 2010, 10 pages.

Miklavcic, D. et al. "Electroporation-Based Technologies and Treatments," The Journal of Membrane Biology (2010) 236:1-2, 2 pgs.

Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.

Murphy, J. V. et al., "Frostbite: Pathogenesis and Treatment" The Journal of Trauma: Injury, Infection, and Critical Care, vol. 48, No. 1, Jan. 2000, pp. 171-178.

Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.

Nagle, W. A. et al. "Cultured Chinese Hamster Cells Undergo Apoptosis After Exposure to Cold but Nonfreezing Temperatures," Cryobiology 27, 1990, pp. 439-451.

Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.

Nanda, G.S. et al., "Studies on electroporation of thermally and chemically treated human erythrocytes," Bioelectrochemistry and Bioenergetics, 34, 1994, pp. 129-134, 6 pgs.

Narins, D.J. et al. "Non-Surgical Radiofrequency Facelift", The Journal of Drugs in Dermatology, vol. 2, Issue 5, 2003, pp. 495-500.

Nielsen, B. "Thermoregulation in Rest and Exercise," Acta Physiologica Scandinavica Supplementum, vol. 323 (Copenhagen 1969), pp. 7-74.

Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.

Nurnberger, F. "So-Called Cellulite: An Invented Disease," Journal of Dermatologic Surgery and Oncology, Mar. 1978, pp. 221-229.

Pease, G. R. et al., "An Integrated Probe for Magnetic Resonance Imaging Monitored Skin Cryosurgery," Journal of Biomedical Engineering, vol. 117, Feb. 1995, pp. 59-63.

Pech, P. et al., "Attenuation Values, Volume Changes and Artifacts in Tissue Due to Freezing," Acta Radiologica,vol. 28, Issue 6, 1987, pp. 779-782.

Peterson, L. J. et al., "Bilateral Fat Necrosis of the Scrotum," Journal of Urology, vol. 116, 1976, pp. 825-826.

Phinney, S. D. et al., "Human Subcutaneous Adipose Tissue Shows Site-Specific Differences in Fatty Acid Composition," The American Journal of Clinical Nutrition, vol. 60, 1994, pp. 725-729.

Pierard, G.E. et al., "Cellulite: From Standing Fat Herniation to Hypodermal Stretch Marks," The American Journal of Dermatology, vol. 22, Issue 1, 2000, pp. 34-37, [Abstract].

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly (ethylene glycol) and Poly (ethylene oxide)," http://www.sigmaaldrich.com/materials-science/materialscience-;products.htmi?TablePage=2020411 0, accessed Oct. 19, 2012.

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

Vallerand et al. "Cold Stress Increases Lipolysis, FFA Ra and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell-Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

(56) References Cited

OTHER PUBLICATIONS

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zelickson, B. et al., "Cryolipolysis for Noninvasive Fat Cell Destruction: Initial Results from a Pig Model", 35 Dermatol. Sug., 2009, pp. 1-9.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

TREATMENT SYSTEMS, METHODS, AND APPARATUSES FOR IMPROVING THE APPEARANCE OF SKIN AND PROVIDING OTHER TREATMENTS

CROSS-REFERENCE TO RELATED APPLICATIONS

The present application is a divisional of U.S. patent application Ser. No. 14/611,127, (now U.S. Pat. No. 10,201, 380), filed Jan. 30, 2015, which claims priority under 35 U.S.C. § 119(e) to U.S. Provisional Application Ser. No. 61/943,250, filed Feb. 21, 2014, U.S. Provisional Application Ser. No. 61/934,549, filed Jan. 31, 2014, and U.S. Provisional Application Ser. No. 61/943,257, filed Feb. 21, 2014, the disclosures of which are incorporated herein by reference in their entireties.

INCORPORATION BY REFERENCE OF COMMONLY-OWNED APPLICATIONS AND PATENTS

The following commonly assigned U.S. patent Applications and U.S. patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Pat. No. 8,337,539 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Pat. No. 9,132,031 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Pat. No. 8,523,927 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Pat. No. 8,603,073 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Pat. No. 8,702,774 entitled "DEVICE, SYSTEM AND METHOD FOR REMOVING HEAT FROM SUBCUTANEOUS LIPID-RICH CELLS";

U.S. Pat. No. 8,676,338 entitled "COMBINED MODALITY TREATMENT SYSTEMS, METHODS AND APPARATUS FOR BODY CONTOURING APPLICATIONS";

U.S. Pat. No. 9,314,368 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Pat. No. 9,844,461 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. Pat. No. 9,545,523 entitled "MULTI-MODALITY TREATMENT SYSTEMS, METHODS AND APPARATUS FOR ALTERING SUBCUTANEOUS LIPID-RICH TISSUE"; and U.S. Pat. No. 9,844,460 entitled "TREATMENT SYSTEMS WITH FLUID MIXING SYSTEMS AND FLUID-COOLED APPLICATORS AND METHODS OF USING THE SAME".

TECHNICAL FIELD

The present disclosure relates generally to treatment devices, methods, and apparatuses for affecting targeted tissue. In particular, several embodiments are directed to treatment systems, methods, and apparatuses for improving the appearance of skin or for providing for other patient treatments.

BACKGROUND

Rhytide (e.g., wrinkles) can affect the appearance of skin on the face and other areas of the body and may be an indicator of age. For example, wrinkles may be present around the eyes, mouth, forehead, neck, hands, etc. As the skin naturally ages, cell division reduces, skin loosens, and skin sags. Age-related wrinkling of the skin can be promoted and/or exacerbated by habitual facial expressions or sleeping patterns, as well as poor hydration. Exposure to ultraviolet radiation and tobacco smoke can accelerate the skin's aging process and result in premature wrinkling. Wrinkles, loose sagging skin, poor skin tone or texture, and other skin abnormalities are often considered to be visually unappealing and have proved to be difficult and vexing problems to treat, although the demand for effective treatments has been and remains quite high. A need exists for more effective treatments of these conditions and other conditions. Accordingly, it is an objective of various embodiments of the present invention to address these and other needs.

BRIEF DESCRIPTION OF THE DRAWINGS

In the drawings, identical reference numbers identify similar elements or acts.

DETAILED DESCRIPTION

A. Overview

Figure 1A:
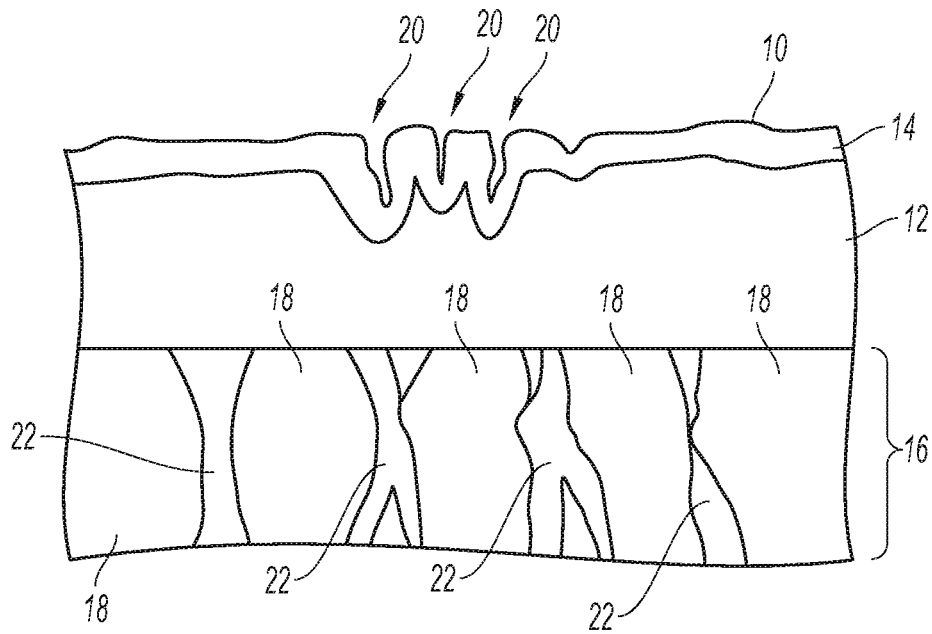
FIG. 1A is a schematic cross-sectional view of tissue with an undesirable appearance.

The present disclosure describes treatment systems and methods for improving the appearance of tissue and other treatments. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the technology but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. The headings provided herein are for convenience only and are not intended to limit or interpret the scope or meaning of the technology.

At least some embodiments are directed to reducing or eliminating wrinkles, loose skin, sagging skin, poor skin tone or texture, and other skin irregularities often considered to be cosmetically unappealing. Some embodiments are directed to skin tightening and/or improving the appearance of cellulite. As used herein, the term "improving the appearance of skin" is intended to include any combination of skin tightening, improving skin tone or texture, thickening of the skin, elimination or reducing fine lines and wrinkles or deeper wrinkles, increasing skin smoothness, improving the appearance of cellulite, or other similar effects. What is not included in the term is treating the skin to such an extent as to cause hyperpigmentation (skin darkening) and/or hypopigmentation (skin lightening) either immediately after the treatment or hours or a day or days or weeks thereafter. Treatment systems disclosed herein can improve skin appearance by causing skin tightening, thickening of tissue (e.g., thickening of the epidermis, dermis, and/or subcutaneous tissue), and/or inducing a cold shock response at the cellular level so as to improve skin tone, skin texture, and/or skin smoothness. In one embodiment, a treatment system has an applicator configured to be applied to a subject's face to treat wrinkles around the eyes, mouth, forehead, etc. The applicator can cool facial tissue to reduce the number of visible wrinkles, reduce the size of wrinkles (e.g., depths, lengths, etc.), or the like. Conformable or contoured applicators can be applied to highly contoured regions around the eyes to reduce or eliminate, for example, crow's feet wrinkles. Treatment systems can also have applicators configured to be applied to other locations along the subject's body. The shape, configuration, mechanical properties, and cooling capabilities of the applicators can be selected based on the tissue characteristics at the treatment site.

Various aspects of the technology are directed to non-invasive applicators that cool the epidermis, dermis, and/or other tissue for a period of time selected to localize thermal effects in targeted tissue while preventing thermal effects in deeper non-targeted tissue. Oftentimes, but not always, target tissue can be intermediate (not surface and not deep) tissue. For example, when treating the face, it is often undesirable to injure the subcutaneous layer beneath the skin, which acts as a support layer for the skin. Additionally, when treating the face and other body areas, it is desirable to minimize or control injury to the epidermis. In an extreme case, if the epidermis is overly frozen, hyperpigmentation (skin darkening) or hypopigmentation (skin lightening) can result, which is often undesirable. At least some embodiments are methods and apparatuses for non-invasively cooling relatively shallow tissue located along the face, neck, hands, hips, buttock, thighs, etc. Targeted tissue be cooled to a temperature equal to or below about −40° C., −35° C., −30° C., −25° C., −20° C., −10° C., or −5° C. for a treatment period equal to or longer than 1 second, 2 seconds, 3 seconds, 5 seconds, 30 seconds, 1 minute, a few minutes, or the like. In some embodiments, targeted epidermal and/or dermal tissue can be cooled to a temperature between about −40° C. and about 0° C., between about −35° C. and about 0° C., between about −30° C. and about 0° C., between about −25° C. and about 0° C., or between about −20° C. and about 0° C. In some embodiments, the treatment period can be exceed about 1 minute, 5 minutes, or 20 minutes, or other periods of time selected based on the treatment to be performed. In some embodiments, the treatment period can be shorter than about 1 minute, 5 minutes, 10 minutes, 20 minutes, 30 minutes, or 1 hour. In some procedures, the surface of the patient's skin is cooled to a temperature equal to or greater than about −40° C., −35° C., −30° C. −25° C., −20° C., −10° C., −5° C., or 0° C. Non-targeted tissue may be subcutaneous adipose tissue, epidermal tissue, or other non-targeted tissue that remains at a higher temperature or is otherwise protected, such as by use of one or more cryoprotectants.

In some embodiments, a thermoelectric applicator can cool the patient's skin to produce a cooling zone in the epidermal and/or dermal layers. As such, cooling can be localized in the epidermis and/or dermis. In some examples, the cooling zone can be at a maximum depth equal to or less than about 2.5 mm. In one procedure, a central region of the cooling zone (e.g., a zone where the most tissue injury is created) can be at a maximum depth of about 0.25 mm to about 1 mm, about 0.25 mm to about 1.5 mm, about 0.25 mm to about 2 mm, about 0.5 mm to about 1.5 mm, about 0.5 mm to about 2 mm, about 0.5 mm to about 2.5 mm, or about 0.5 mm to about 3 mm. In some procedures, the depth of the cooling zone and depth of the most significant tissue injury can be at a equal to or less than about 1 mm, 1.5 mm, 2 mm, 2.5 mm, or 3 mm. In some procedures for treating areas with thin skin (e.g., facial skin around the eyes), the cooling zone can be located at a depth equal to or less than about 1 mm, 0.25 mm, 0.5 mm, 1 mm, or 1.5 mm.

Various aspects of the technology are directed to improving the appearance of skin by cooling a surface of a patient's skin to produce at least a cooling event (e.g., a partial freeze event, total freeze event, etc.). The cooling event can be detected, and a cooling device can be controlled to continue cooling the patient's skin so as to maintain a frozen state of targeted tissue for a desired period of time. In one procedure, the tissue can be kept in a partially or totally frozen state for longer than about, for example, about 1 second, 5 seconds, 10 seconds, 20 seconds, 30 seconds, 1 minute, several minutes, or other time period selected to reduce or limit frostbite or necrosis.

In certain embodiments, methods for affecting skin of a human subject's body include positioning an applicator of a cooling apparatus on the subject and removing heat from a treatment site to affect the appearance of the subject's skin without causing an appreciable reduction of subcutaneous adipose tissue. A sufficient amount of thermal energy can be removed from the site so as to reduce wrinkles by, for example, reducing the number of visible wrinkles and/or sizes of the wrinkles. In other embodiments, a sufficient amount of thermal energy is removed from the treatment site so as to tighten skin at the treatment site, or in further embodiments, to alter the tissue between a surface of the skin and subcutaneous lipid-rich cells of the subject's body. In a further embodiment, tissue is cooled to induce fibrosis that increases the firmness of tissue at the treatment site. Fibrosis can be induced in the epidermis, dermis, and/or subcutaneous tissue. Vacuum applicators can stretch or otherwise mechanically alter skin to increase damage and fibrosis in the skin.

At least some aspects of the technology are directed to treatment methods for affecting a target region of a human subject's body to alter an appearance of a treatment site by removing heat using a cooling apparatus to alter at least one of skin tightness, smoothness, or skin surface irregularities. The methods can include removing a sufficient amount of heat to produce fibrosis that alters the subject's skin. In certain embodiments, the fibrosis increases the tightness of the skin and/or increases the smoothness of the surface of the skin. Other embodiments of the technology are directed to methods of cooling tissue using a cooling apparatus to produce a cold shock response for affecting proteins that alter the appearance of the subject's skin. The proteins can be heat shock proteins, cold shock proteins, and/or stress response proteins. In one embodiment, tissue can be cooled to a temperature for increasing a protein synthesis rate of one or more of the proteins.

At least some embodiments of the technology are directed to freezing skin to induce injury to the skin. An applicator can be placed at a treatment site on the subject and can remove heat from the subject's skin to controllably freeze the skin to control the freeze injury (or trauma) to the skin. The freeze injury can improve tissue appearance by, for example, tightening of the skin, thickening of the skin, and/or inducing a cold shock response at the cellular level. In some procedures, most of the skin located between the applicator and subcutaneous tissue can experience at least partial freezing. With or without freezing, at least some embodiments of the technology are directed to controlling the cooling device or providing other means for sufficiently protecting the epidermis from injury to an extent that causes hyperpigmentation (skin darkening) or hypopigmentation (skin lightening). The other means can include heating the epidermis to a non-freezing temperature while deeper tissue remains cold to induce injury thereto, and/or applying a cryoprotectant to a surface of the skin to provide freeze protection to the epidermis while allowing deeper tissue to be more affected by the cooling/cold treatment.

In further embodiments of the technology, damage to tissue (e.g., dermis and/or subcutaneous tissue) can be reduced or eliminated by applying a substance to the subject's skin. In other embodiments, tissue damage can be limited by applying energy to non-targeted tissue while cooling the treatment site. For example, electromagnetic energy, infrared energy, microwave energy, radiofrequency energy, ultrasound energy, electrical energy (e.g., AC or DC electric fields), and/or light can be delivered to the subject's skin to supply energy thereto. In certain arrangements, the applied energy can inhibit the reduction of subcutaneous lipid-rich cells while the treatment site is cooled by the applicator.

Some aspects of the technology are directed to treatment methods for affecting tissue of a human subject's body by cooling tissue to produce a freeze event that affects at least one of skin tone, thickness of the tissue layers (e.g., dermal layer and/or epidermal layer), and/or tissue elasticity. In certain embodiments, the method also includes inhibiting damage to non-targeted tissue of the subject's skin while producing the freeze event. The freeze event can include injury to at least some of the subject's skin (e.g., epidermis, dermis, etc.), subcutaneous adipose tissue, or other targeted tissue.

Devices and systems that enable target tissue supercooling are also described. A freezing point of a material is most reliably ascertained by warming frozen material slowly and measuring a temperature at which melting begins to occur. This temperature is generally not ambiguous if the material is slowly warmed. Partial melting will begin to occur at the freezing/melting point. Conversely, if a non-frozen material is cooled, its freezing/melting point is harder to ascertain since it is known that many materials can simply "supercool," that is they can be cooled to a bulk temperature below their freezing/melting point and still remain in a non-frozen state. As used herein, "supercooling," "supercooled," "supercool," etc., refers to a condition in which a material is at a temperature below its freezing/melting point but is still in an unfrozen or mostly unfrozen state.

Tissue can be supercooled by controllably cooling the surface of the skin for altering and reducing adipose tissue, body contouring and augmentation, treating of acne, treating hyperhidrosis, or other cryotherapy applications. Aspects of the disclosure are further directed to methods and devices that provide protection of non-targeted cells, such as non-lipid-rich cells (e.g., in the dermal and/or epidermal skin layers), by preventing or limiting freeze damage during dermatological and related aesthetic procedures that require sustained exposure to cold temperatures. For example, treatment systems and devices for performing cryotherapy methods can be configured to control thermal parameters such that body fluids within the treatment site are supercooled to temperatures below the freezing point without forming or nucleating ice crystals. The supercooled body fluids can then be intentionally nucleated to damage, reduce, disrupt, or otherwise affect the targeted cells. Nucleation can be induced by delivering an alternating current to the tissue, applying a nucleating solution onto the surface of the skin (for example one that includes bacteria which initiate nucleation), and/or by creating a mechanical perturbation to the tissue, such as by use of vibration, ultrasound energy, etc.

Some of the embodiments disclosed herein can be for cosmetically beneficial alterations of a variety of body regions. As such, some treatment procedures may be for the sole purpose of altering the body region to conform to a cosmetically desirable look, feel, size, shape or other desirable cosmetic characteristic or feature. Accordingly, at least some embodiments of the cosmetic procedures can be performed without providing any, or in another embodiment, providing minimal therapeutic effect. For example, some treatment procedures may be directed to treatment goals that do not include restoration of health, physical integrity, or the physical well-being of a subject. In other embodiments, however, the cosmetically desirable treatments may have therapeutic outcomes (whether intended or not), such as, psychological benefits, alteration of body hormones levels (by the reduction of adipose tissue), etc. The cosmetic methods can target regions of a subject's skin to change a subject's appearance. In another embodiment, the methods can target skin irregularities, wrinkles, sebaceous glands to treat acne, sweat glands to treat hyperhidrosis, hair follicles to injure and remove hair, or other targeted cells to change a subject's appearance or address a therapeutic condition.

B. Treatment Sites

FIG. 1A is a schematic cross-sectional view of tissue with skin 10 having wrinkles 20 (e.g., folds, ridges, or creases) that may be located, for example, along the face, legs (e.g., thighs, buttock, etc.), or other locations. The dimensions (e.g., depths, lengths, etc.) of the wrinkles 20 can vary by body location and typically increase over time. Wrinkles 20 typically affect the epidermis 14 and dermis 12 layers of the skin; however, the subdermal adipose and connective tissue can also play a role in the appearance of skin irregularities. For example, loss of adipose or fat cells 18 and/or weakened connective tissue 22 in the subcutaneous layers (e.g., subdermal tissue 16) can increase the appearance of wrinkles 20 in the skin 10.

Figure 1B:
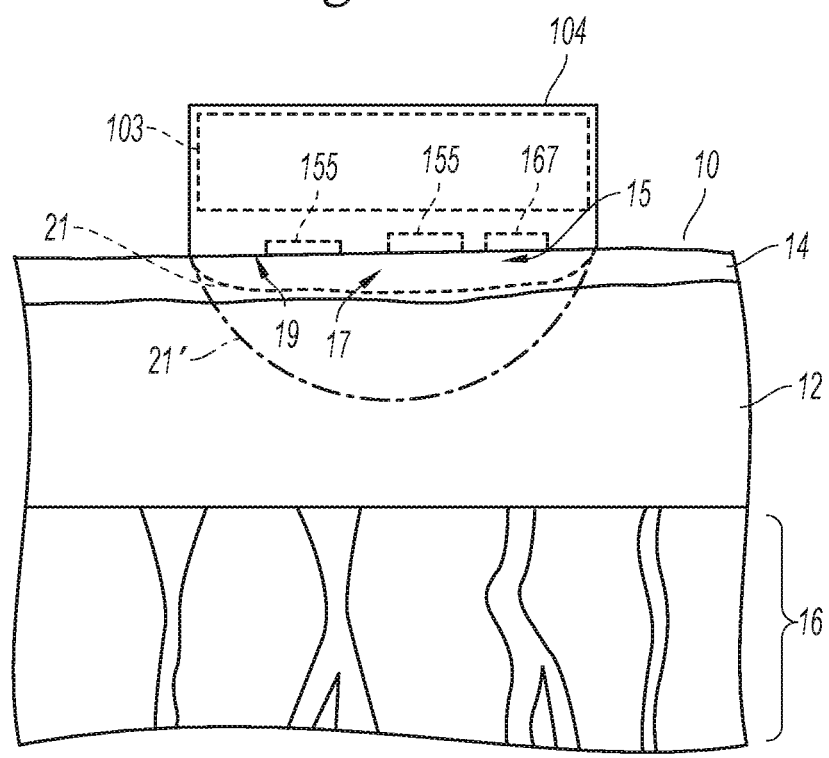
FIG. 1B is a schematic cross-sectional view of the tissue in FIG. 1A with an improved appearance. An applicator is in thermal contact with the surface of the skin.

FIG. 1B is a schematic cross-sectional view of the skin 10 of the subject in FIG. 1A with improved appearance. An illustrated treatment device in the form of a thermoelectric applicator 104 ("applicator 104") has affected tissue (e.g., skin 10, epidermis 14, dermis 12, or other targeted tissue) to reduce or eliminate the wrinkles, improve skin tone and/or texture, increase skin smoothness, and/or improve the appearance of cellulite. The applicator 104 can perform different cryotherapy procedures designed to make the skin 10 substantially free of visible irregularities.

In one example, a heat-exchanging surface 19 of the applicator 104 can be in thermal contact with a surface of the skin 10. A cooling device 103 of the applicator 104 can cool a treatment site 15 and affect tissue at a cooling zone 21 (shown in phantom line). A central region 17 of the cooling zone 21 can be at a maximum depth of, for example, about 0.25 mm to about 2 mm, about 0.25 mm to about 1 mm, about 0.5 mm to about 1 mm, or about 0.5 mm to about 2 mm. The depth of the cooling zone 21 can be selected to avoid injuring deeper subcutaneous tissue (e.g., subdermal tissue 16). In one procedure, the cooling zone 21 comprises mostly epidermal tissue. In another procedure, the cooling device 103 cools and affects tissue in the cooling zone 21' (shown in dashed-dot line) which comprises mostly epidermal and dermal tissue. Adjacent tissue (e.g., subcutaneous tissue) may also be cooled but can be at a sufficiently high temperature to avoid thermal injury. In some procedures, the cooling zone 21' can comprise most of the tissue located directly between the cooled heat-exchanging surface 19 and the subcutaneous tissue (e.g., dermal tissue 16). For example, at least about 60%, 70%, 80%, 90%, or 95% of the tissue directly between the heat-exchanging surface 19 and the subcutaneous tissue can be located within the cooling zone 21'.

C. Cryotherapy

Figure 2:
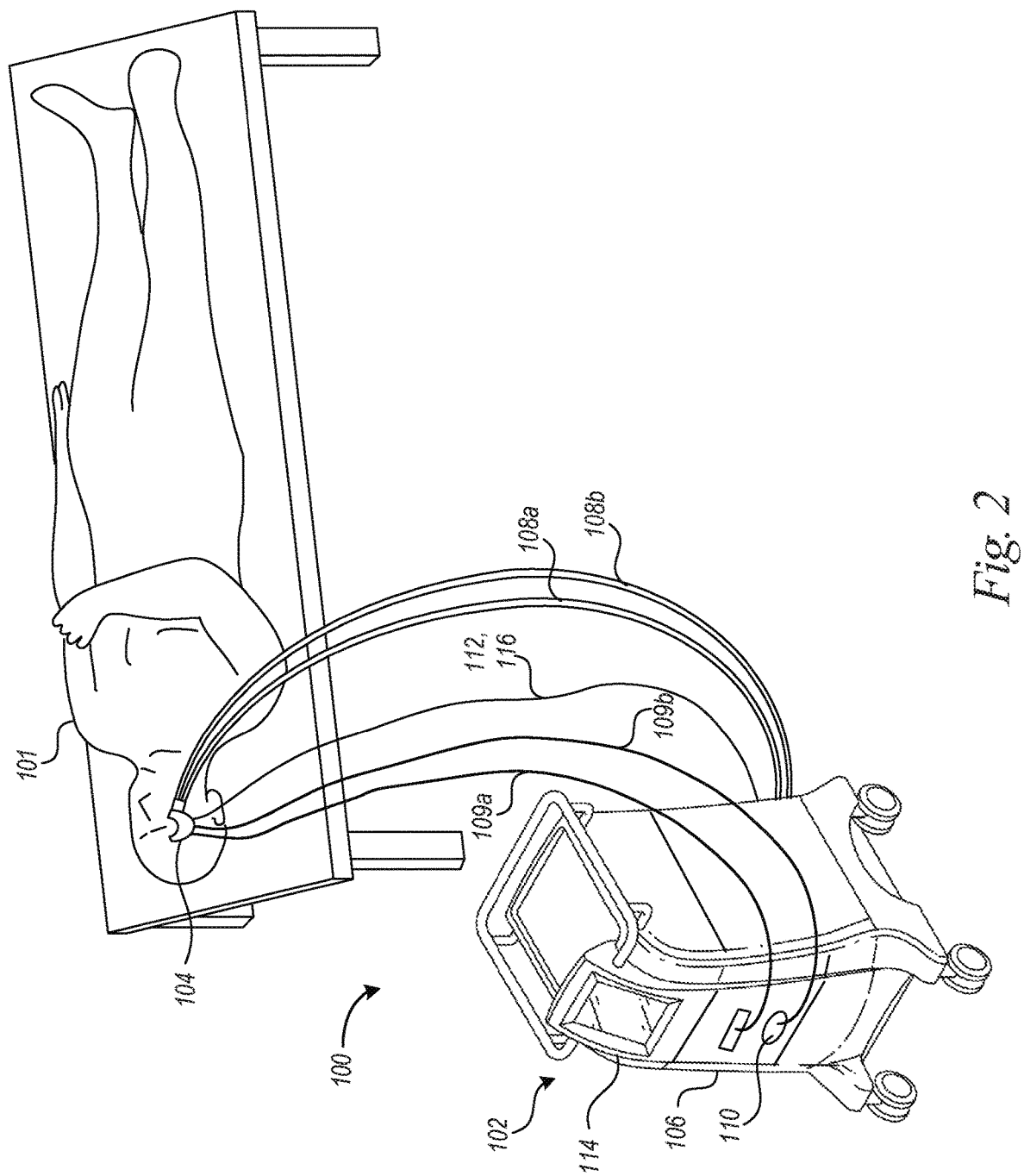
FIG. 2 is a partially schematic isometric view of a treatment system for improving the appearance of facial skin in accordance with an embodiment of the disclosure.

FIG. 2 and the following discussion provide a general description of an example of a suitable non-invasive treatment system 100 in which aspects of the technology can be implemented. The treatment system 100 can be a temperature-controlled cooling apparatus for cooling tissue at a targeted treatment site to perform cryotherapy. Tissue characteristics affected by cryotherapy can include, without limitation, tissue strength, tissue elasticity, cell size, cell number, and/or tissue layer thickness. For example, the treatment system 100 can cool the epidermis, dermis, or other targeted tissue to reduce or eliminate skin irregularities. Non-targeted tissue, such as subdermal tissue, can remain generally unaffected. In one embodiment, cryotherapy can increase the thicknesses of multiple tissue layers. In one example, cooling can produce a cold shock response to increase the thicknesses of the epidermis and/or dermis by affecting protein proliferation and other cellular functions. Those skilled in the relevant art will appreciate that other examples of the disclosure can be practiced with other treatment systems and treatment protocols, including invasive, minimally invasive, and other non-invasive medical treatments.

The applicator 104 is suitable for altering a human subject's skin without affecting subcutaneous tissue (e.g., subcutaneous adipose tissue and lipid-rich cells, etc.). The applicator 104 can be suitable for reducing wrinkles (e.g., wrinkles 20 of FIG. 1A), loose skin, sagging skin, or other skin surface irregularities by cooling the skin without permanently altering cells of non-targeted tissue (e.g., deep dermal tissue, subdermal tissue, etc.). Without being bound by theory, the effect of cooling selected cells (e.g., cells of the skin, layers of epidermis, etc.) is believed to result in, for example, protein alteration (e.g., synthesis of heat shock proteins, stress proteins, etc.), cell size alteration, cell division, wound remodeling (e.g., thickening of the epidermis, contraction of the epidermis, etc.), fibrosis, and so forth. By cooling the skin to a sufficient low temperature, target cells that contribute to the presence of undesired features can be selectively affected while non-targeted tissue can be unaffected.

The applicator 104 can be used to perform a wide range of different cryotherapy procedures. One cryotherapy procedure involves at least partially or totally freezing tissue to form crystals that alter targeted cells to cause skin tightening, skin thickening, fibrosis, etc. without destroying a significant amount of cells in the skin. To avoid destroying skin cells, the surface of the patient's skin can be cooled to temperatures no lower than, for example, −40° C. for a duration short enough to avoid, for example, excessive ice formation, permanent thermal damage, or significant hyperpigmentation or hypopigmentation (including long-lasting or permanent hyperpigmentation or hypopigmentation). In another embodiment, destruction of skin cells can be avoided by applying heat to the surface of the patient's skin to heat the skin cells above their freezing temperature. The patient's skin can be warmed to at least about −30° C., −25° C., −20° C., −15° C., −10° C., 0° C., 10° C., 20° C., 30° C., or other temperature sufficient to avoid, for example, excessive ice formation, permanent thermal damage, or significant hyperpigmentation or hypopigmentation of the non-targeted and/or epidermal tissue. In some treatments, skin can be cooled to produce partial freeze events that cause apoptotic damage to skin tissue without causing significant damage to adjacent subcutaneous tissue. Apoptosis, also referred to as "programmed cell death", of the skin tissue can be a genetically-induced death mechanism by which cells slowly self-destruct without incurring damage to surrounding tissues. Other cryotherapy procedures may cause non-apoptotic responses.

In some tissue-freezing procedures, the applicator 104 can controllably freeze tissue and can optionally detect the freeze event (or other event). After detecting the freeze event, the applicator 104 can periodically or continuously remove heat from the target tissue to keep a volume of target tissue frozen or partially frozen for a suitable length of time to elicit a desired response. The detected freeze event can be a partial freeze event, a complete freeze event, etc. In some embodiments, the controlled freezing causes tightening of the skin, thickening of the skin, and/or a cold shock response at the cellular level in the skin. In one tissue-freezing treatment, the applicator 104 can produce a partial or total freeze event that includes, without limitation, partial or full thickness freezing of the patient's skin for a relatively short time limit to avoid cooling the adjacent subcutaneous tissue to a low enough temperature for subcutaneous cell death or undue injury to the subcutaneous layer. The freezing process can include forming ice crystals in intracellular and/or extracellular fluids, and the ice crystals can be small enough to avoid disrupting membranes so as to prevent significant permanent tissue damage, such as necrosis. Some partial freeze events can include freezing mostly extracellular material without freezing a substantial amount of intercellular material. In other procedures, partial freeze events can include freezing mostly intercellular material without freezing a substantial amount of extracellular material. The frozen target tissue can remain in the frozen state long enough to affect the target tissue but short enough to avoid damaging non-targeted tissue. For example, the duration of the freeze event can be shorter than about 20 seconds, 30 seconds, or 45 seconds or about 1, 2, 3, 4, 5 or 10 minutes. The frozen tissue can be thawed to prevent necrosis and, in some embodiments, can be thawed within about 20 seconds, 30 seconds, or 45 seconds or about 1, 2, 3, 4, 5, or 10 minutes after initiation of the freeze event.

In several embodiments, tissue can be cooled to induce cold shock cellular responses in the region of the subject being treated are a desirable outcome for beneficially alter (e.g., smoothing and/or tightening) the skin. Without being bound by theory, it is believed that exposure to cold induces a stress response cascade in the interrogated cells that results in the immediate synthesis of cytoprotective genes. Among these are genes that code for heat shock proteins and/or chaperone proteins involved in protein folding. Heat shock proteins can help alter a cell's phenotype by either impeding, protecting or promoting protein function both during the acute response to stress as well as to subsequent stresses. Cold shock proteins (e.g., cold-inducible RNA-binding protein (CIRP) that may have roles in cellular proliferation and inflammation) have also been identified in mammalian cells. Induction of cold shock cellular responses can dramatically change a cell's proteome to promote cellular survival under environmental interrogation and/or following cold-induced tissue injury. It has been observed in mammalian cells that cold stress can alter the lipid composition of the cellular membranes, as well as change rates of protein synthesis and cell proliferation. Without being bound by theory, the selective effect of cooling on target cells (e.g., epidermal and/or dermal cells) is believed to result in, for example, changes in cellular metabolism, proliferation, survivability, wound healing, wound contraction and other cellular responses that can improve tissue characteristics at the treatment site.

The mechanisms of cold-induced tissue injury in cryotherapy can also involve direct cellular injury (e.g., damage to the cellular machinery) and/or vascular injury. For example, cell injury can be controlled by adjusting thermal parameters, including (1) cooling rate, (2) end (or minimum) temperature, (3) time held at the minimum temperature (or hold time), (4) temperature profile, and (5) thawing rate. In one example, increasing the hold time can allow the intracellular compartments to equilibrate with the extracellular space, thereby increasing cellular dehydration. Another mechanism of cold-induced injury is cold and/or freeze-stimulated immunologic injury. Without being bound by theory, it is believed that after cryotherapy, the immune system of the host is sensitized to the disrupted tissue (e.g., lethally damaged tissue, undamaged tissue, or sublethally injured tissue), which can be subsequently destroyed by the immune system.

During an inflammatory phase of healing following cold-induced injury, platelets are among the first cells to appear at the treatment site. Platelets release platelet derived growth factor (PDGF), which upregulates soluble fibrinogen production. Fibrinogen is converted to insoluble strands of fibrin which form a matrix for the influx of monocytes and fibroblasts. During a proliferative phase of healing, cellular activity promotes epithelialization and fibroplasia. Fibronectin, produced initially from plasma, promotes epidermal migration by providing its own lattice. In freeze wounds, basal keratinocytes secrete collagenase-1 when in contact with fibrillar collagen, and collagenase-1 disrupts attachment to fibrillar collagen which allows for continued migration of keratinocytes into the treatment site. It is during the proliferative phase that a healing process following injury can result in a thicker epidermal layer with increased cellular activity.

In additional embodiments, induction of fibrosis (e.g., the formation of fibrous connective tissue) in the region of the subject being treated is a desirable outcome for beneficially altering the skin. For example, fibrosis can increase the amount of connective tissue in a desired tissue layer (e.g., epidermis, dermis, and/or subcutaneous tissue) to increase a firmness of the tissue. In some embodiments, increased firmness of the tissue can increase the tightness and/or the smoothness of the surface of the skin. Without being bound by theory, cooling temperatures can result in inflammation of the interrogated tissue. Immune cells, such as macrophages, release transforming growth factor beta (TGF-β) which stimulates the proliferation and activation of fibroblast cells. Migrating and activated fibroblast cells deposit connective tissue, including collagen and glycosaminoglycans that can thicken and/or strengthen the affected tissue. Such thickening and/or firming of the affected tissue can beneficially alter skin characteristics by reducing the appearance of wrinkles, fine lines, loose skin, etc.

The system 100 can also perform treatments to affect subcutaneous tissue by cooling the subject's skin for a period of time long enough so that lipid-rich cells in a subcutaneous layer are substantially affected. This can be desired particularly when treating non-facial areas, such as the thighs, arms, abdomen etc., where a skin tightening effect is desired as well as a volumetric reduction, which is aided by altering subcutaneous lipid rich cells. The term "subcutaneous tissue" means tissue lying beneath the dermis and includes subcutaneous fat, or adipose tissue, which is composed primarily of lipid-rich cells, or adipocytes. It is believed that shallow tissue can be cooled to improve skin appearance while also cooling subcutaneous tissue to cause, for example, apoptosis. Apoptosis of subcutaneous lipid-rich cells may be a desirable outcome for beneficially altering (e.g., sculpting and/or reducing) adipose tissue that may contribute to an undesirable appearance. Apoptosis of subcutaneous lipid-rich cells can involve ordered series of biochemical events that induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990). One aspect of apoptosis, in contrast to cellular necrosis (a traumatic form of cell death causing, and sometimes induced by, local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response.

Without being bound by theory, one mechanism of apoptotic lipid-rich cell death by cooling is believed to involve localized crystallization of lipids within the adipocytes at temperatures that may or may not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other possible mechanisms of adipocyte damage, described in U.S. Pat. No. 8,192,474, relates to ischemia/reperfusion injury that may occur under certain conditions when such cells are cooled as described herein. For instance, during treatment by cooling as described herein, targeted adipose tissue may experience a restriction in blood supply and thus be starved of oxygen due to isolation while pulled into, e.g., a vacuum cup, or simply as a result of the cooling which may affect vasoconstriction in the cooled tissue. In addition to the ischemic damage caused by oxygen starvation and the build-up of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., electromagnetic, thermal, electrical, chemical, mechanical, acoustic or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may also exist.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

Without being bound by theory, the effect of cooling on lipid-rich cells is believed to result in, for example, membrane disruption, shrinkage, disabling, destroying, removing, killing, or another method of lipid-rich cell alteration. For example, when cooling the subcutaneous tissues to a temperature lower than 37° C., subcutaneous lipid-rich cells can selectively be affected. In general, the cells in the epidermis and dermis of the subject 101 have lower amounts of lipids compared to the underlying lipid-rich cells forming the subcutaneous tissues. Since lipid-rich cells are more sensitive to cold-induced damage than non-lipid-rich epidermal or dermal cells, it is possible to use non-invasive or minimally invasive cooling to destroy lipid-rich cells without destroying the overlying skin cells. In some embodiments, lipid-rich cells are destroyed while the appearance of overlying skin is improved.

Deep hypodermal fat cells are more easily damaged by low temperatures than the overlying dermal and epidermal layers of skin, and as such, thermal conduction can be used to cool the desired layers of skin to a temperature above the freezing point of water, but below the freezing point of fat. It is believed that the temperatures can be controlled to manage damage in the epidermis and/or dermis via, for example, intracellular and/or extracellular ice formation. Excessive ice formation may rupture the cell wall and may also form sharp crystals that locally pierce the cell wall as well as vital internal organelles. Ice crystal initiation and growth can be managed to avoid cell death in the skin. When extracellular water freezes to form ice, the remaining extracellular fluid becomes progressively more concentrated with solutes. The high solute concentration of the extracellular fluid may cause intracellular fluid to be driven through the semi-permeable cellular wall by osmosis resulting in cell dehydration. The applicator 104 can reduce the temperature of the deep lipid-rich cells such that the deep lipid rich cells are destroyed while the temperature of the upper and surface skin cells are maintained at a high enough temperature to produce non-destructive freeze events in the skin. Cryoprotectants and/or thermal cycling can prevent destructive freeze events in the skin and limit injury to the skin cells.

D. Treatment Systems and Methods of Treatment

FIG. 2 is a partially schematic isometric view of the non-invasively treatment system 100 for performing cryotherapy procedures disclosed herein. The term "treatment system", as used generally herein, refers to cosmetic or medical treatment systems. The components of the treatment system 100 can be selected and implemented in various embodiments to apply selected treatment profiles to the subject 101 (e.g., a human or an animal) for improving the appearance of the treatment site. The treatment system 100 can include a treatment unit or tower 102 ("treatment tower 102") connected to the applicator 104 by supply and return fluid lines 108a-b and power-lines 109a-b.

The applicator 104 can have one or more cooling devices powered by electrical energy delivered via the power-lines 109a-b. A control line 116 can provide communication between electrical components of the applicator 104 and a controller 114 of the treatment tower 102. The cooling devices of the applicator 104 can be cooled using coolant that flows between the applicator 104 and the treatment tower 102 via the supply and return fluid lines 108a-b. In one example, the applicator 104 has a cooling device (e.g., cooling device 103 of FIG. 1B) with one or more thermoelectric cooling elements and fluid channels through which the coolant flows to cool the thermoelectric cooling elements. The thermoelectric cooling elements can include heat-exchanging plates, Peltier devices, or the like. In one embodiment, the applicator 104 can be a non-thermoelectric device that is heated/cooled using only coolant. The applicator 104 can include sensors configured to measure tissue impedance, treatment application force, and/or tissue contact. As described herein, sensors can be used to monitor tissue and, in some embodiments, detect freeze events. Applicators configured to be applied to facial tissue can have pressure sensors to monitor applied pressures to maintain a desired level of comfort. The number and types of sensors can be selected based on the treatment to be performed.

The treatment tower 102 can include a chiller unit or module 106 ("chiller unit 106") capable of removing heat from the coolant. The chiller unit 106 can include one or more refrigeration units, thermoelectric chillers, or any other cooling devices and, in one embodiment, includes a fluid chamber configured to house the coolant that is delivered to the applicator 104 via the fluid lines 108a-b. In some procedures, the chiller unit 106 can circulate warm coolant to the applicator 104 during periods of warming. In certain procedures, the chiller unit 106 can alternatingly provide heated and chilled coolant. The circulating coolant can include water, glycol, synthetic heat transfer fluid, oil, a refrigerant, or any other suitable heat conducting fluid. Alternatively, a municipal water supply (e.g., tap water) can be used in place of or in conjunction with the treatment tower 102. The fluid lines 108a-b can be hoses or other conduits made of polyethylene, polyvinyl chloride, polyurethane, and/or other materials that can accommodate the particular coolant. One skilled in the art will recognize that there are a number of other cooling technologies that could be used such that the treatment unit, chiller unit, and/or applicator(s) need not be limited to those described herein. Additional features, components, and operation of the treatment tower 102 are discussed in connection with FIG. 6.

FIG. 2 shows the applicator 104 positioned to treat crow's feet wrinkles near the patient's right eye. Feedback data from sensors of the applicator 104 can be collected in real-time because real-time processing of such feedback data can help correctly and efficaciously administer treatment. In one example, real-time data processing is used to detect freeze events and to control the applicator 104 to continue cooling the patient's skin after the partial or total freeze event is detected. Tissue can be monitored to keep the tissue in the frozen state (e.g., at least partially or totally frozen state) for a period of time. The period of time can be selected by the treatment tower 102 or an operator and can be longer than about, for example, 10 seconds, 30 seconds, 1 minute, or a few minutes. Other periods of time can be selected if needed or desired. The applicator 104 can include sensors configured to measure tissue impedance, force/pressure applied to the subject 101, optical characteristics of tissue, and/or tissue contact temperatures. As described herein, sensors can be used to monitor tissue and, in some embodiments, to detect freeze events. The number and types of sensors can be selected based on the treatment to be performed.

The applicator 104 can be used at other treatment sites and can be replaced with other applicators. Applicators can be configured to treat identified portions of the patient's body, such as the face, neck, chin, cheeks, arms, pectoral areas, thighs, calves, buttocks, abdomen, "love handles", back, hands, and so forth. For example, mask applicators can be used to cover the subject's face. Conformable applicators can be applied along the face, neck, or other highly contoured regions. By way of another example, vacuum applicators may be applied at the back region, and belt applicators can be applied around the thigh region, either with or without massage or vibration as discussed in connection with FIG. 9. Exemplary applicators and their configurations usable or adaptable for use with the treatment system 100 variously are described in, e.g., U.S. Pat. No. 8,834,547 and commonly assigned U.S. Pat. No. 7,854,754 and U.S. Patent Publication Nos. 2008/0077201, 2008/0077211, and 2008/0287839, which are incorporated by reference in their entireties.

In further embodiments, the system 100 of FIG. 2 may also include a patient protection device (not shown) incorporated into or configured for use with the applicator 104 that prevents the applicator from directly contacting a patient's skin and thereby reduces the likelihood of cross-contamination between patients and minimizes cleaning requirements for the applicator. The patient protection device may also include or incorporate various storage, computing, and communications devices, such as a radio frequency identification (RFID) component, to monitor and/or meter use. Exemplary patient protection devices are described in commonly assigned U.S. Patent Publication No. 2008/0077201.

In operation, and upon receiving input to start a treatment protocol, the controller 114 can cycle through each segment of a prescribed treatment plan. In so doing, power supply 110 and chiller unit 106 can provide power and coolant to one or more functional components of the applicator 104, such as thermoelectric coolers (e.g., TEC "zones"), to begin a cooling cycle and, in some embodiments, activate features or modes such as vibration, massage, vacuum, etc. The controller 114 can monitor treatment by receiving temperature readings from temperature sensors that are part of the applicator 104 or proximate to the applicator 104, the patient's skin, a patient protection device, etc. It will be appreciated that while a target region of the body has been cooled or heated to the target temperature, in actuality that region of the body may be close but not equal to the target temperature, e.g., because of the body's natural heating and cooling variations. Thus, although the system 100 may attempt to heat or cool the tissue to the target temperature or to provide a target heat flux, a sensor may measure a sufficiently close temperature or heat flux. If the target temperature has not been reached, power can be increased or decreased to change heat flux to maintain the target temperature or "set-point" selectively to affect targeted tissue. The system 100 can thus monitor the treatment site while accurately cooling/heating tissue to perform the methods discussed herein.

Figure 3:
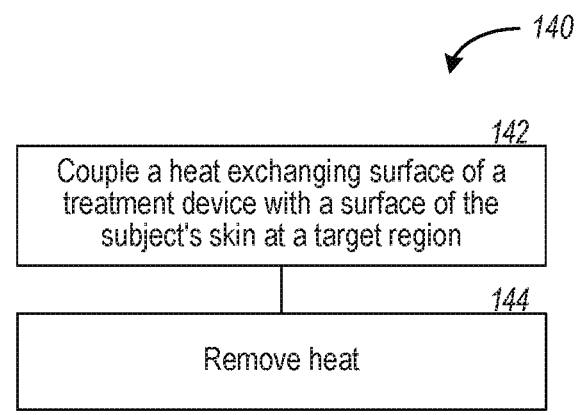
FIGS. 3 to 5B are flow diagrams illustrating methods for improving the appearance of skin in accordance with embodiments of the technology.

FIG. 3 is a flow diagram illustrating a method 140 for improving the appearance of a subject's skin in accordance with embodiments of the disclosure. An early stage of the method 140 can include coupling a heat-exchanging surface of a treatment device with the surface of the subject's skin at a target region (block 142). FIG. 1B shows the heat-exchanging surface 19 in the form of an exposed surface of a heat-exchanging plate of the applicator 104. In another embodiment, the heat-exchanging surface 19 can be the surface of an interface layer or a dielectric layer. Coupling of the heat-exchanging surfaces to the skin can be facilitated by using restraining means, such as a belt or strap. In other embodiments, a vacuum or suction force can be used to positively couple the treatment device to the patient's skin. In some methods, a thermally conductive substance can couple the heat-exchanging surface 19 to the patient's skin and can optionally be a cryoprotectant. Suitable and preferred cryoprotectants are described in commonly assigned U.S. Patent Publication No. 2007/0255362.

At block 144, heat is removed from tissue for a period of time that may vary depending on the location of the treatment site and may induce cold shock, freeze tissue, injure tissue, etc. Thermal injuries can induce fibrosis that increases the firmness and/or tone of the tissue. In some cold shock procedures, the subject's skin can be cooled to produce a cold shock response which affects proteins, such as heat shock proteins, cold shock proteins, and/or stress response proteins. In some embodiments, the subject's skin can be cooled to a temperature no lower than about −40° C., −30° C., −20° C., −10° C. to produce the cold shock response. Additionally or alternatively, the treatment site can be cooled to a temperature selected to increase a protein synthesis rate of one or more of the proteins. Some treatment protocols can include two or more segments each designed to produce cold shocks responses, freeze tissue, or injure tissue. For example, a treatment protocol may alternate between tissue-freeze segments and tissue-thaw segments. In another example, one treatment protocol can be designed to reduce wrinkles (e.g., age-related wrinkles) via shock proteins and another treatment protocol can be designed to tighten loose tissue via fibrosis. Accordingly, different treatment protocols can be used on different parts of a patient's body. Although the method 140 is described with reference to the treatment system 100 of FIG. 2, the method 140 may also be performed using other treatment systems with additional or different applicators, hardware, and/or software components.

Figure 4:
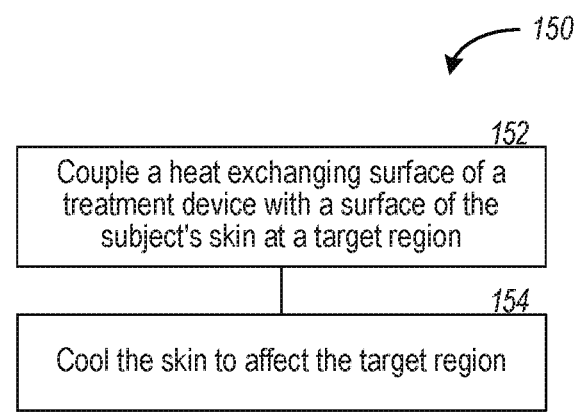

FIG. 4 is a flow diagram illustrating a method 150 for improving the appearance of skin in accordance with embodiments of the disclosure. The method 150 can include coupling a heat-exchanging surface of a treatment device with the surface of the subject's skin at a target region (block 152). At block 154, the method 150 includes cooling the subject's skin to affect tissue at the target region. In one embodiment, the skin's smoothness, thickness, texture, tone, and/or elasticity is improved. In one embodiment, the skin is cooled to induce a freeze-related injury, and in another embodiment, the skin is cooled to induce a cold shock response.

Figure 5A:
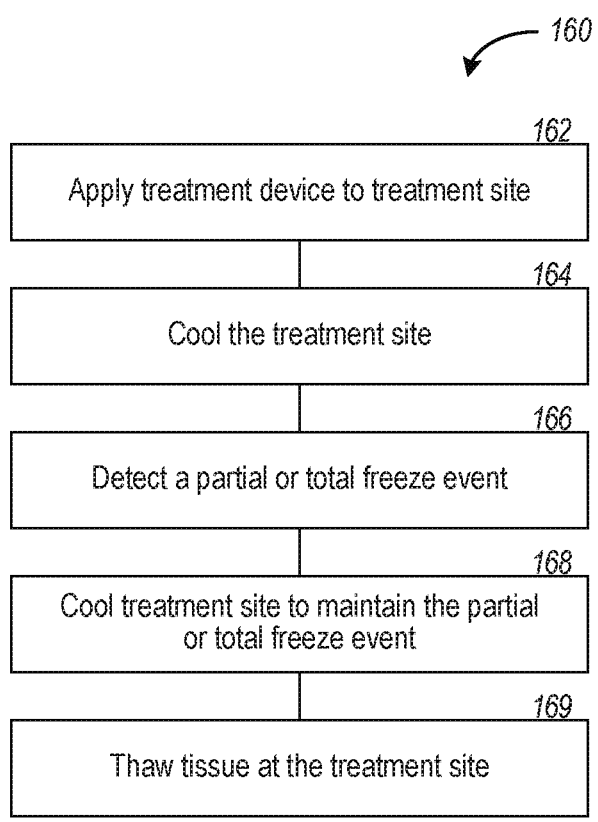

FIG. 5A is a flow diagram illustrating a method 160 for improving the appearance of skin by producing a freeze event in accordance with embodiments of the disclosure. Generally, a treatment device can be applied to a subject and can cool a surface of a patient's skin to produce and detect a freeze event. After detecting the freeze event (or events), operation of the treatment device can be controlled to keep at least a portion of the subject's tissue frozen for a sufficient length of time to improve the appearance of the skin but not so long as to create undue injury to tissue. Details of method 160 are discussed below.

At block 162, the treatment device is applied to a subject by placing a heat-exchanging surface in thermal contact with the subject's skin. In some embodiments, a substance is applied to the subject's skin before applying the treatment device. A substance can be used to (a) provide thermal coupling between the subject's skin and cooling devices (e.g., cooling plates of cooling devices) to improve heat transfer therebetween, (b) selectively protect non-target tissues from freeze damage (e.g., damage due to crystallization), and/or (c) promote freeze events by increasing nucleation sites. The substance may be a fluid, a gel, or a paste and may be hygroscopic, thermally conductive, and biocompatible. In some embodiments, the substance can be a cryoprotectant that reduces or inhibits cell destruction. As used herein, "cryoprotectant," "cryoprotectant agent," and "composition" mean substances (e.g., compositions, formulations, compounds, etc.) that assist in preventing freezing of tissue compared to an absence of the substances(s). In one embodiment, the cryoprotectant allows, for example, the treatment device to be pre-cooled prior to being applied to the subject for more efficient treatment. Further, the cryoprotectant can also enable the treatment device to be maintained at a desired low temperature while preventing ice from forming on a surface (e.g., heat-exchanging surface), and thus reduces the delay in reapplying the treatment device to the subject. Yet another aspect of the technology is that the cryoprotectant may prevent the treatment device from freezing to the skin of the patient or subject. Additionally or alternatively, the cryoprotectant can allow microscopic crystals to form in the tissue but can limit crystal growth that would cause cell destruction and, in some embodiments, allows for enhanced uptake or absorption and/or retention in target tissue prior to and during the introduction of cooling.

Some embodiments according to the present technology may use a cryoprotectant with a freezing point depressant that can assist in preventing freeze damage that would destroy cells. Suitable cryoprotectants and processes for implementing cryoprotectants are described in commonly-assigned U.S. Patent Publication No. 2007/0255362. The cryoprotectant may additionally include a thickening agent, a pH buffer, a humectant, a surfactant, and/or other additives and adjuvants as described herein. Freezing point depressants may include, for example, propylene glycol (PG), polyethylene glycol (PEG), dimethyl sulfoxide (DMSO), or other suitable alcohol compounds. In a particular embodiment, a cryoprotectant may include about 30% propylene glycol, about 30% glycerin (a humectant), and about 40% ethanol. In another embodiment, a cryoprotectant may include about 40% propylene glycol, about 0.8% hydroxyethyl cellulose (a thickening agent), and about 59.2% water. In a further embodiment, a cryoprotectant may include about 50% polypropylene glycol, about 40% glycerin, and about 10% ethanol. The freezing point depressant may also include ethanol, propanol, iso-propanol, butanol, and/or other suitable alcohol compounds. Certain freezing point depressants (e.g., PG, PPG, PEG, etc.) may also be used to improve spreadability of the cryoprotectant and to provide lubrication. The freezing point depressant may lower the freezing point of body liquids/lipids to about 0° C. to −50° C., about 0° C. to −50° C., or about 0° C. to −30° C. In other embodiments the freezing point of the liquids/lipids can be lowered to about −10° C. to about −40° C., about −10° C. to about −30° C., or to about −10° C. to about −20° C. In certain embodiments, the freezing point of the liquids/lipids can be lowered to a temperature below about 0° C., below about −5° C., below about −10° C., below about −12° C., below about −15° C., below about −20° C., below about −30° C., or below about −35° C. For example, the freezing point depressant may lower the freezing point of the liquids/lipids to a temperature of about −1° C. to about −40° C., about −5° C. to about −40° C., or about −10 to about −40° C.

Cryoprotectant can be intermittently or continuously delivered to the surface of the patient's skin for a period of time which is short enough to not significantly inhibit the initiation of the partial or total freeze event in dermal tissue but is long enough to provide substantial protection to non-targeted tissue (e.g., subcutaneous adipose tissue). The rate of cryoprotectant delivery can be selected based on the characteristics of the cryoprotectant and the desired amount of tissue protection. In one specific treatment process, an interface member is placed directly over the target area, and the treatment device with a disposable sleeve or liner is placed in contact with the interface member. The interface member can be a cotton pad, gauze pad, a pouch, or a container with a reservoir containing a volume of cryoprotectant or other flowable conductive substance. The interface member can include, for example, a non-woven cotton fabric pad saturated with the substance that delivers cryoprotectant at a desired delivery rate. Suitable pads include Webril™ pads manufactured by Covidien of Mansfield, Mass. Further details regarding the interface member and associated systems and methods are described in commonly-assigned U.S. Patent Publication No. 2010/0280582.

Figure 5B:
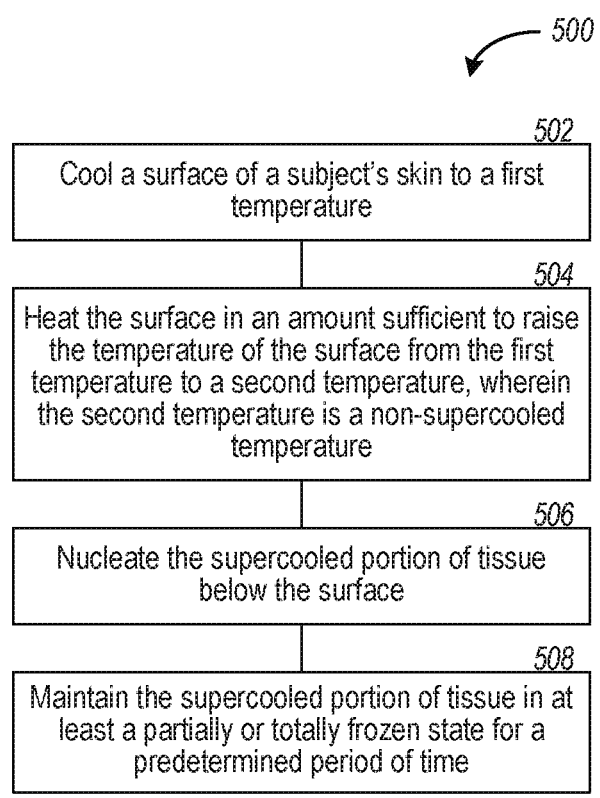

In a certain embodiment, the system 100 (FIG. 2) can be used to perform several treatment methods without using a chemical cryoprotectant. FIG. 5B is a flow diagram illustrating a method 500 for improving the appearance of skin without any chemical composition in accordance with embodiments of the disclosure. As shown in FIG. 5B, an early stage of the method 500 can include cooling a surface of a human subject's skin to a first temperature (block 502). The first temperature can be, for example, between about −5° C. and −40° C. such that a portion of tissue below the surface is in a supercooled state. The supercooled tissue can include epidermal tissue, dermal tissue, subcutaneous tissue, other tissue, and combinations thereof.

The method 500 can also include heating the surface of the human subject's skin in an amount sufficient to raise the temperature of the surface or upper layer of tissue from the first temperature to a second temperature that is a non-supercooled temperature. Deeper tissue below the surface can remain in the supercooled state (block 504). For example, the treatment system can be used to heat the surface (e.g., an upper portion of the epidermis) of the skin to a temperature greater than about 0° C. while underlying tissue remains supercooled. In some embodiments, tissue of the skin at a depth of less than about 0.2 mm, 0.5 mm, or 1 mm are warmed to a non-supercooled state. The temperature of the skin surface can be increased about 40° C., 30° C. 20° C., 10° C. during the warming period (e.g., 0.5 second, 1 second, 2 seconds, 5 seconds, etc.). The surface of the skin can be periodically heated to minimize or limit thermal damage while deeper tissue is at or below the treatment temperature (e.g., a temperature for supercooling).

In block 506, the method 500 can further include nucleating the supercooled portion of tissue below warmed tissue to cause at least some cells in the supercooled tissue to at least partially freeze. In one embodiment, nucleation of the supercooled tissue is caused by a mechanical perturbation (e.g., vibration, ultrasound pulses, etc.) while warmed cells residing at the surface of the human subject's skin do not freeze. This allows for localized nucleation and protection of cells at the surface can be accomplished without the use of a chemical cryoprotectant. Optionally, a cryoprotectant may also be used to provide further protection for epidermal tissue to minimize any undue damage thereto which might result in a hyperpigmentation or hypopigmentation response sometime after completing treatment. In various embodiments, the supercooled tissue can comprise some portion of the epidermal tissue (e.g., a lower region of epidermal tissue), dermal tissue, connective tissue, subcutaneous tissue, or other tissue targeted to experience a freeze injury.

In certain embodiments, the method 500 may further include maintaining the supercooled tissue in at least a partially or totally frozen state for a predetermined period of time (block 508). For example, the supercooled tissue can be maintained in the at least partially or totally frozen state for longer than about 2 seconds, 5 seconds, 10 seconds, 12 seconds, 15 seconds, or 20 seconds. In various arrangements, the supercooled tissue can be maintained in the at least partially or totally frozen state for a duration of time sufficient to improve an appearance of skin or provide for other treatments (e.g., tightening the skin, increasing skin smoothness, thickening the skin, improving the appearance of cellulite, improving acne, improving a quality of hair, improving a condition associated with hyperhidrosis, etc.). In certain embodiments, the maintaining the freeze event can include detecting a temperature of the portion of tissue and controlling the cooling and heating to maintain at least a portion of the tissue in at least a partially or totally frozen state for the predetermined time (e.g., greater than about 10 seconds, greater than about 12 seconds, greater than about 15 seconds, or greater than about 20 seconds).

Referring back to FIG. 5A, and at block 164, the treatment device can rapidly cool the surface of the patient's skin to a sufficiently low temperature to cause a partial or total freeze event in targeted tissue. The rapid cooling can create a thermal gradient with the coldest temperatures near the applicator (e.g., the upper layers of skin). The resulting thermal gradient causes the temperature of the upper layer(s) of the skin to be lower than that of the targeted deeper cells. This allows the skin to be frozen for a short enough duration so that temperature equilibrium is not established across the skin and adjacent subcutaneous tissue, typically adipose tissue. A cryoprotectant and/or warming cycle can be used to inhibit freezing the uppermost non-targeted layer, or layers, of skin, particularly epidermal tissue, so as to prevent or minimize any chance of creating hyperpigmentation or hypopigmentation.

A partial freeze event can include at least some crystallization (e.g., formation of microscopic ice crystals) in intercellular material (e.g., fluid, cell components, etc.) and/or extracellular fluid. By avoiding extensive ice crystal formation that would cause frostbite or necrosis, partial freeze events can occur without undesired tissue damage. In addition, total freeze events can be created which are maintained for a period of time which is kept short enough so as to not cause an undesired amount of tissue damage. In some embodiments, the surface of the patient's skin can be cooled to a temperature no lower than about −40° C., −30° C., −20° C., −10° C., or −5° C. to produce a partial or total freeze event in the skin without causing irreversible skin damage. For example, the treatment system 100 of FIG. 2 can cool the skin to a temperature in a range from about −40° C. to about 0° C. In another example, the surface of the patient's skin can be cooled to from about −40° C. to about 0° C., from about −30° C. to about 0° C., from about −20° C. to about −5° C., or from about −15° C. to about −5° C. In further examples, the surface of the patient's skin can be cooled to below about −10° C., or in yet another embodiment, from about −25° C. to about −15° C. It will be appreciated that the skin surface can be cooled to other temperatures based on the mechanism of action.

To perform cryotherapy, the cooling period can be sufficiently short to minimize, limit, or substantially eliminate necrosis, or other unwanted thermal damage, due to the freeze event. In one procedure, the applicator (e.g., applicator 104 of FIGS. 1B and 2) can produce a freeze event that begins within a predetermined period of time after the applicator begins cooling the patient's skin or after the freeze event begins. The predetermined period of time can be equal to or less than about 30, 60, 90, 120, or 150 seconds and, in some embodiments, the predetermined period of time can be from about 30 seconds to about 150 seconds. A controller (e.g., controller 114 of FIG. 2) can select the predetermined period of time based on the treatment temperatures, treatment sites, and/or cryotherapy to be performed. Alternatively, an operator can select the period of time for cooling and can enter it into the controller 114.

To help initiate the freeze event (e.g., the partial or total freeze event), a substance, energy, and/or pressure can be used to aid in the formation of nucleation sites for crystallization. Substances that promote nucleation can be applied topically before and/or during skin cooling. The energy for promoting nucleation can include, without limitation, acoustic energy (e.g., ultrasound energy), mechanical energy (e.g., vibratory motion, massaging, and/or pulsatile forces), or other energy. The energy can also comprise alternating current electrical energy. A nucleating substance can also optionally be applied to the skin. The applicators disclosed herein can include one or more actuators (e.g., motors with eccentric weights), vibratory motors, hydraulic motors, electric motors, pneumatic motors, solenoids, piezoelectric shakers, and so on for providing mechanical energy, pressure, etc. Pressure for promoting nucleation can be applied uniformly or non-uniformly across the treatment site. The applicators can also include AC electrodes. For example, the applicator 104 of FIG. 1B can include one or more elements 155 in the form of actuators, motors, solenoids, piezoelectric shakers, transducers (e.g., ultrasound transducers), electrodes (e.g., electrical electrodes, RF electrodes, etc.), or combinations thereof. Substances that promote nucleation can be applied topically before and/or during skin cooling.

At block 166, the treatment device can detect the partial or total freeze event in the patient's skin using one or more electrical components. FIG. 1B shows the applicator 104 with an electronic component in the form of a sensor 167 that can identify positive (increase) or negative (decrease) temperature changes. During cooling, targeted tissue can reach a temperature below the freezing point of its biological tissue and fluids (e.g., approximately −1.8° C.). As tissue, lipids, and fluids freeze, crystals can form and energy associated with the latent heat of crystallization of the tissue is released. A relatively small positive change in tissue temperature can indicate a partial freeze event whereas a relatively large positive change in tissue temperature can indicate a complete freeze event. The sensor 167 (FIG. 1B) can detect the positive change in tissue temperature, and the treatment system can identify it as a freeze event. The treatment system can be programmed to prevent small variations in temperature from causing false alarms with respect to false treatment events. Additionally or alternatively, the treatment system disclosed herein may detect changes in the temperature of its components or changes in power supplied to the treatment device (e.g., treatment devices receive more power from the system to provide additional cooling). For example, the sensor 167 can detect changes in temperature of the applicator 104 as the applicator gets colder in order to cool the tissue warmed by crystallization.

Referring now to FIG. 2, the system 100 can monitor the location and/or movement of the applicator 104 and may prevent false or inaccurate determinations of treatment events based on such monitoring. The applicator 104 may move during treatment which may cause the applicator 104 to contact a warmer area of skin, to no longer contact the skin, and so on. This may cause the system 100 to register a difference in temperature that is inconsistent with a normal treatment. The controller 114 may be programmed to differentiate between these types of temperature increases and a temperature increase associated with a treatment event. U.S. Pat. No. 8,285,390 discloses techniques for monitoring and detecting freeze events and applicator movement and is incorporated by reference in its entirety. Additionally, the treatment system 100 can provide an indication or alarm to alert the operator to the source of this temperature increase. In the case of a temperature increase not associated with a treatment event, the system 100 may also suppress false indications, while in the case of a temperature increase associated with freezing, the system 100 take any number of actions based on that detection as described elsewhere herein.

The system 100 can use optical techniques to detect events at block 166 of FIG. 5A. For example, the sensor 167 of FIG. 1B can be an optical sensor capable of detecting changes in the optical characteristics of tissue caused by freezing. The optical sensor can include one or more energy emitters (e.g., light sources, light emitting diodes, etc.), detector elements (e.g., light detectors), or other components for non-invasively monitoring optical characteristics of tissue. In place of or in conjunction with monitoring using optical techniques, tissue can be monitored using electrical and/or mechanical techniques because changes in electrical impedance and/or mechanical properties of the tissue can be detected and may indicate freezing of tissue. In embodiments for measuring electrical impedance, the sensor 167 (FIG. 1B) can include two electrodes that can be placed in electrical communication with the skin for monitoring electrical energy traveling between the electrodes via the tissue. In embodiments for measuring mechanical properties, the sensor 167 can comprise one or more mechanical sensors which can include, without limitation, force sensors, pressure sensors, and so on.

At block 168, the partial or total freeze event can be maintained by continuously or periodically cooling the patient's tissue to keep a target volume of skin frozen for a period of time, which can be long enough to affect the skin and thereby improve skin appearance. In short treatments, the period of time can be equal to or shorter than about 5, 10, 15, 20, or 25 seconds. In longer treatments, the period of time can be equal to or longer than about 25 seconds, 30 seconds, 45 seconds or 1, 2, 3, 4, 5, or 10 minutes. In some procedures, the applicator 104 of FIGS. 1B and 2 can be controlled so that the skin is partially or completely frozen for no longer than, for example, 5 minutes, 10 minutes, 20 minutes, 30 minutes, 45 minutes, or 1 hour. In some examples, the skin is frozen for about 1 minute to about 5 minutes, about 5 minutes to about 10 minutes, about 10 minutes to about 20 minutes, or about 20 minutes to about 30 minutes. The length of time the skin is kept frozen can be selected based on severity of the freeze injury.

At block 168 of FIG. 5A, the treatment system can control the applicator so that the partial or total freeze event causes apoptotic damage to the target tissue and does not cause necrotic damage to non-targeted tissue. The cooling period can be sufficiently short to avoid or limit permanent tissue damage and, in some embodiments, can be less than about, for example, 5 minutes, 10 minutes, 15 minutes, 20 minutes, 25 minutes, 30 minutes, 35 minutes, 40 minutes, 45 minutes, 50 minutes, 55 minutes, or 1 hour. In one example, the applicator produces a partial freeze event short enough to prevent establishing equilibrium temperature gradients in the patient's skin. This allows freezing of shallow targeted tissue without substantially affecting deeper non-targeted tissue. Moreover, cells in the dermal tissue can be affected to a greater extent than the cells in the subcutaneous layer. For example, skin cells can be reduced in size or number to a greater extent than subcutaneous cells, including lipid-rich cells. In some procedures, the subcutaneous layer can be kept at a sufficiently high temperature (e.g., at or above 0° C.) to prevent any freeze event in the subcutaneous layer while the shallower skin tissue experiences the partial or total freeze event. Cryoprotectant can be used to protect the subcutaneous layer. Topical cryoprotectants can be absorbed by the skin and can ultimately reach the subcutaneous layer. Cryoprotectant can be injected directly into the subcutaneous layer before performing the cooling cycle.

In some embodiments, the freeze event can occur in the epidermal layer to injure, reduce, or disrupt the epidermal cells without substantially injuring, reducing, or disrupting dermal cells and/or subcutaneous cells. In other embodiments, the freeze event can occur in the dermal layer to injure, reduce, or disrupt dermal cells without substantially injuring, reducing, or disrupting epidermal cells and/or subcutaneous cells. A cryoprotectant can be used to protect the epidermal layer to avoid causing long-lasting or permanent hyperpigmentation or hypopigmentation. For example, a cryoprotectant can be delivered to the surface of the patient's skin for a period of time which is short enough to not significantly inhibit the initiation of the partial or total freeze event in dermal tissue, but the period of time can be long enough to provide substantial protection to epidermal tissue. The cryoprotectant can prevent permanent hyperpigmentation or hypopigmentation of epidermal tissue due to tissue cooling, and the cryoprotectant delivery time and rate can be selected based on the cryoprotectant's ability to protect tissue. In one embodiment, the cryoprotectant prevents hyperpigmentation or hypopigmentation of the skin surface and also prevents damage of the epidermal tissue due to tissue cooling. In yet other embodiments, the freeze event can occur in the epidermal and dermal layers to injure, reduce, or disrupt the epidermal and dermal cells without substantially injuring, reducing, or disrupting subcutaneous tissue to avoid body contouring. Such treatments are well suited for improving the appearance of skin along the face, including wrinkled, loose, and/or sagging skin around the eyes and mouth.

Certain treatment protocols can include sequentially targeting different layers. A first treatment session can target the epidermal layer and a subsequent additional treatment sessions can target the other layers. Different layers can be targeted in a different protocol.

The treatment system can also control operation of the applicator to thermally injure the patient's skin to cause fibrosis, which increases the amount of connective tissue in a desired tissue layer (e.g., epidermis and/or dermis) to increase the firmness and appearance of the skin. In other treatments, the treatment system controls the applicator to supercool at least a portion of tissue below the skin layer. A perturbation (e.g., a mechanical perturbation) can be used to nucleate the supercooled tissue to at least partially or totally freeze the tissue. Alternating electric fields can be used to create nucleation perturbations. Various substances can be applied to the treatment site to facilitate nucleation of supercooled tissue.

At block 169, the patient's partially or completely frozen skin can be thawed by heating it in order to minimize, reduce, or limit tissue damage. The applicator (e.g., applicator 104 of FIG. 2) can thaw the patient's skin, or other frozen tissue, after the freeze event occurs and after a period of time has transpired. The period of time can be equal to or shorter than about 5, 10, 15, 20, or 25 seconds or about 1, 2, 3, 4, 5, or 10 minutes. In one example, the uppermost skin layer(s) can be periodically heated to a temperature above the skin's freezing point to provide freeze protection thereto. The thermal elements can be resistive heaters, electromagnetic energy emitters, Peltier devices, etc. In some embodiments, the applicator 104 of FIGS. 1B and 2 can have cooling elements and separate heating elements that can cooperate to provide precise temperature control of freezing and thawing/warming cycles. Alternatively, the applicator 104 may stop or reduce tissue cooling to allow cooled tissue to naturally warm and thaw. Thus, tissue can be actively or passively thawed.

The applicator 104 (FIG. 2) can thaw the patient's skin, or other frozen tissue, after the freeze event occurs and after the period of time has transpired to reduce and control freeze damage. In one example, the uppermost skin layer can be periodically heated to a temperature above the skin's freezing point to provide freeze protection thereto. In some procedures, the applicator 104 repeatedly freezes and thaws tissue to control thermal injuries to that tissue.

The system 100 can be used to perform several different cryotherapy procedures. Although specific methods are described in connection with FIGS. 3-5B, one skilled in the art is capable of identifying other methods that the system 100 could perform. Additionally, the treatment system 100 of FIG. 6 can perform the methods described in connection with FIGS. 3-5B. Applicators are discussed in connection with FIGS. 7-9 and can be used with the system 100 (FIGS. 2 and 6) or different treatment systems to perform the procedures disclosed herein.

Figure 6:
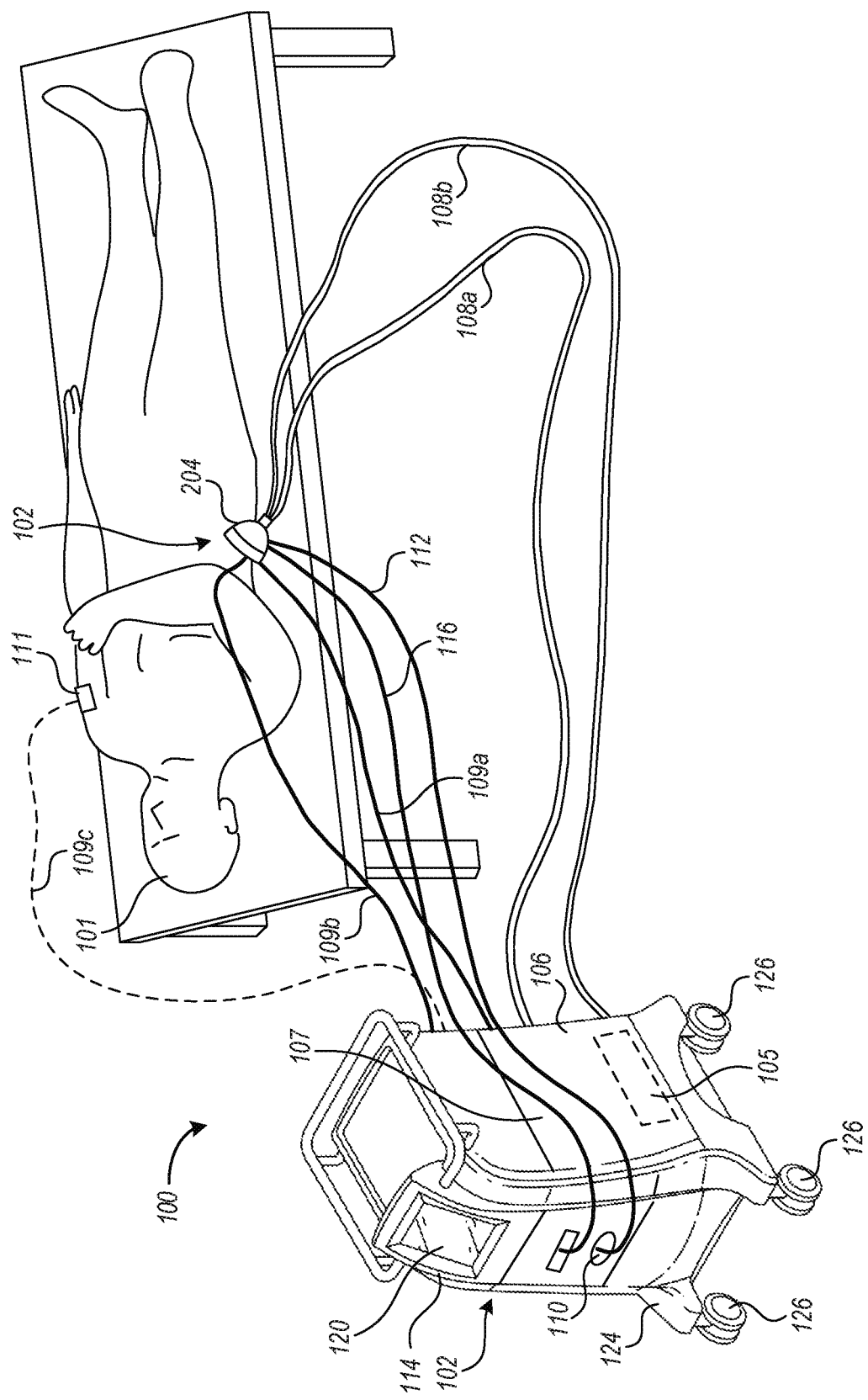
FIG. 6 is a partially schematic isometric view of a treatment system treating tissue located along a subject's torso in accordance with an embodiment of the disclosure.

FIG. 6 is a partially schematic isometric view of the system 100 with a multi-modality applicator 204 positioned along the subject's waist. The power supply 110 can provide a direct current voltage to the applicator 204 to remove heat from the subject 101. The controller 114 can monitor process parameters via sensors (e.g., sensors of the applicator 204 and/or sensors placed proximate to the applicator 204) via the control line 116 to, among other things, adjust the heat removal rate and/or energy delivery rate based on a custom treatment profile or patient-specific treatment plan, such as those described, for example, in commonly assigned U.S. Pat. No. 8,275,442.

The controller 114 can exchange data with the applicator 204 via an electrical line 112 or, alternatively, via a wireless or an optical communication link. The control line 116 and electrical line 112 are shown without any support structure. Alternatively, control line 116 and electrical line 112 (and other lines including, but not limited to fluid lines 108a-b and power lines 109a-b) may be bundled into or otherwise accompanied by a conduit or the like to protect such lines, enhance ergonomic comfort, minimize unwanted motion (and thus potential inefficient removal of heat from and/or delivery of energy to subject 101), and to provide an aesthetic appearance to the system 100. Examples of such a conduit include a flexible polymeric, fabric, composite sheath, an adjustable arm, etc. Such a conduit (not shown) may be designed (via adjustable joints, etc.) to "set" the conduit in place for the treatment of the subject 101.

The controller 114 can receive data from an input/output device 120, transmit data to a remote output device (e.g., a computer), and/or exchange data with another device. The input/output device 120 can include a display or touch screen (shown), a printer, video monitor, a medium reader, an audio device such as a speaker, any combination thereof, and any other device or devices suitable for providing user feedback. In the embodiment of FIG. 6, the input/output device 120 can be a touch screen that provides both an input and output functionality. The treatment tower 102 can include visual indicator devices or controls (e.g., indicator lights, numerical displays, etc.) and/or audio indicator devices or controls. These features can be part of a control panel that may be separate from the input/output device 120, may be integrated with one or more of the devices, may be partially integrated with one or more of the devices, may be in another location, and so on. In alternative examples, input/output device 120 or parts thereof (described herein) may be contained in, attached to, or integrated with the applicator 204.

The controller 114, power supply 110, chiller unit 106 with a reservoir 105, and input/output device 120 are carried by a rack 124 with wheels 126 for portability. In alternative embodiments, the controller 114 can be contained in, attached to, or integrated with the multi-modality applicator 204 and/or a patient protection device. In yet other embodiments, the various components can be fixedly installed at a treatment site. Further details with respect to components and/or operation of applicators, treatment tower, and other components may be found in commonly-assigned U.S. Patent Publication No. 2008/0287839.

The system 100 can include an energy-generating unit 107 for applying energy to the target region, for example, to further interrogate cooled or heated cells via power-lines 109a-b. In one embodiment, the energy-generating unit 107 can be a pulse generator, such as a high voltage or low voltage pulse generator, capable of generating and delivering a high or low voltage current, respectively, through the power lines 109a, 109b to one or more electrodes (e.g., cathode, anode, etc.) in the applicator 204. In other embodiments, the energy-generating unit 107 can include a variable powered RF generator capable of generating and delivering RF energy, such as RF pulses, through the power lines 109a, 109b or to other power lines (not shown). RF energy can be directed to non-targeted tissue to help isolate cooling. For example, RF energy can be delivered to non-targeted tissue, such as subdermal tissue, to inhibit or prevent damage to such non-targeted tissue. In a further embodiment, the energy-generating unit 107 can include a microwave pulse generator, an ultrasound pulse laser generator, or high frequency ultrasound (HIFU) phased signal generator, or other energy generator suitable for applying energy. In additional embodiments, the system 100 can include more than one energy-generator unit 107 such as any one of a combination of the energy modality generating units described herein. Systems having energy-generating units and applicators having one or more electrodes are described in commonly assigned U.S. Patent Publication No. 2012/0022518 and U.S. patent application Ser. No. 13/830,413.

The applicator 204 can include one or more heat-exchanging units. Each heat-exchanging unit can include or be associated with one or more Peltier-type thermoelectric elements, and the applicator 204 can have multiple individually controlled heat-exchanging zones (e.g., between 1 and 50, between 10 and 45; between 15 and 21, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Applicators having multiple individually controlled heat-exchanging units are described in commonly assigned U.S. Patent Publication Nos. 2008/0077211 and 2011/0238051.

The applicator 204 can be applied with pressure or with a vacuum type force to the subject's skin. Pressing against the skin can be advantageous to achieve efficient treatment. In general, the subject 101 has an internal body temperature of about 37° C., and the blood circulation is one mechanism for maintaining a constant body temperature. As a result, blood flow through the tissue to be treated can be viewed as a heat source that counteracts the cooling of the desired targeted tissue. As such, cooling the tissue of interest requires not only removing the heat from such tissue but also that of the blood circulating through this tissue. Thus, temporarily reducing or eliminating blood flow through the treatment region, by means such as, e.g., applying the applicator with pressure, can improve the efficiency of tissue cooling (e.g., tissue cooling to reduce cellulite, wrinkles, sagging skin, loose skin, etc.), and avoid excessive heat loss. Additionally, a vacuum can pull tissue away from the body which can assist in cooling targeted tissue.

Figure 7:
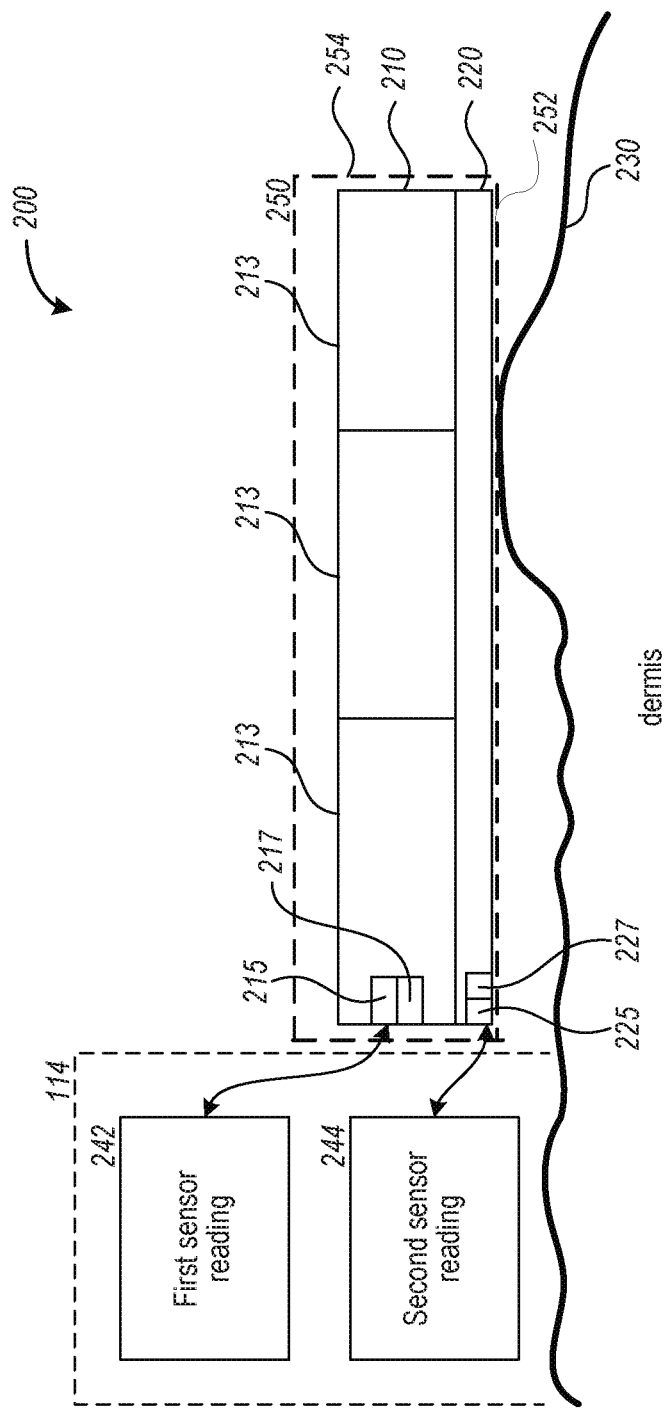
FIG. 7 is a partial cross-sectional view illustrating a treatment device in accordance with embodiments of the technology.

FIG. 7 is a schematic cross-sectional view illustrating a treatment device in the form an applicator 200 for non-invasively removing heat from target tissue in accordance with an embodiment of the present technology. The applicator 200 can include a cooling device 210 and an interface layer 220. In one embodiment, the cooling device 210 includes one or more thermoelectric elements 213 (e.g., Peltier-type TEC elements) powered by the treatment tower (e.g., treatment tower 102 of FIGS. 2 and 6).

The applicator 200 can contain a communication component 215 that communicates with the controller 114 to provide a first sensor reading 242, and a sensor 217 that measures, e.g., temperature of the cooling device 210, heat flux across a surface of or plane within the cooling device 210, tissue impedance, application force, tissue characteristics (e.g., optical characteristics), etc. The interface layer 220 can be a plate, a film, a covering, a sleeve, a substance reservoir or other suitable element described herein and, in some embodiments, may serve as the patient protection device described herein.

The interface layer 220 can also contain a similar communication component 225 that communicates with the controller 114 to provide a second sensor reading 244 and a sensor 227 that measures, e.g., the skin temperature, temperature of the interface layer 220, heat flux across a surface of or plane within the interface layer 220, contact pressure with the skin 230 of the patient, etc. For example, one or both of the communication components 215, 225 can receive and transmit information from the controller 114, such as temperature and/or heat flux information as determined by one or both of sensors 217, 227. The sensors 217, 227 are configured to measure a parameter of the interface without substantially impeding heat transfer between the heat-exchanging plate 210 and the patient's skin 230. The applicator 200 can also contain components described in connection with FIGS. 2 and 6.

In certain embodiments, the applicator 200 can include a sleeve or liner 250 (shown schematically in phantom line) for contacting the patient's skin 230, for example, to prevent direct contact between the applicator 200 and the patient's skin 230, and thereby reduce the likelihood of cross-contamination between patients, minimize cleaning requirements for the applicator 200, etc. The sleeve 250 can include a first sleeve portion 252 and a second sleeve portion 254 extending from the first sleeve portion. The first sleeve portion 252 can contact and/or facilitate the contact of the applicator 200 with the patient's skin 230, while the second sleeve portion 254 can be an isolation layer extending from the first sleeve portion 252. The second sleeve portion 254 can be constructed from latex, rubber, nylon, Kevlar®, or other substantially impermeable or semi-permeable material. The second sleeve portion 254 can prevent contact between the patient's skin 230 and the heat-exchanging plates 210, among other things. Further details regarding a patient protection device may be found in U.S. Patent Publication No. 2008/0077201.

A device (not shown) can assists in maintaining contact between the applicator 200 (such as via an interface layer 220) and the patient's skin 230. The applicator 200 can include a belt or other retention devices (not shown) for holding the applicator 200 against the skin 230. The belt may be rotatably connected to the applicator 200 by a plurality of coupling elements that can be, for example, pins, ball joints, bearings, or other type of rotatable joints. Alternatively, retention devices can be rigidly affixed to the end portions of the interface layer 220. Further details regarding a suitable belt devices or retention devices may be found in U.S. Patent Publication No. 2008/0077211.

A vacuum can assist in forming a contact between the applicator 200 (such as via the interface layer 220 or sleeve 250) and the patient's skin 230. The applicator 200 can provide mechanical energy to a treatment region using the vacuum. Imparting mechanical vibratory energy to the patient's tissue by repeatedly applying and releasing (or reducing) the vacuum, for instance, creates a massage action during treatment. Further details regarding vacuums and vacuum type devices may be found in U.S. Patent Application Publication No. 2008/0287839.

Figure 8A:
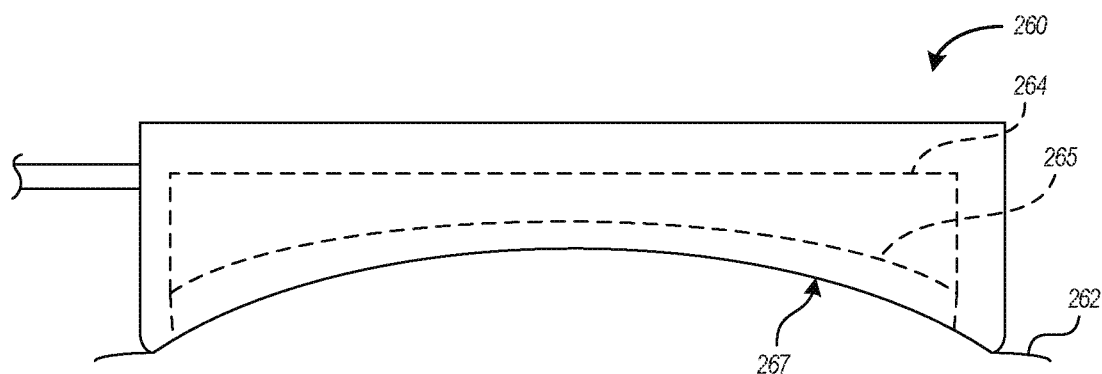
FIGS. 8A to 8C are schematic cross-sectional views illustrating treatment devices in accordance with embodiments of the technology.
Figure 8B:
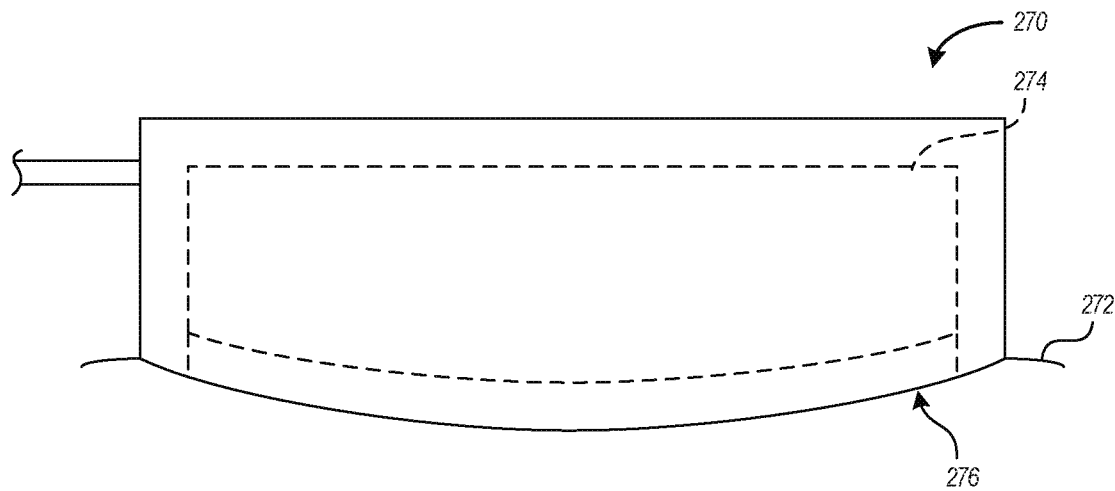
Figure 8C:
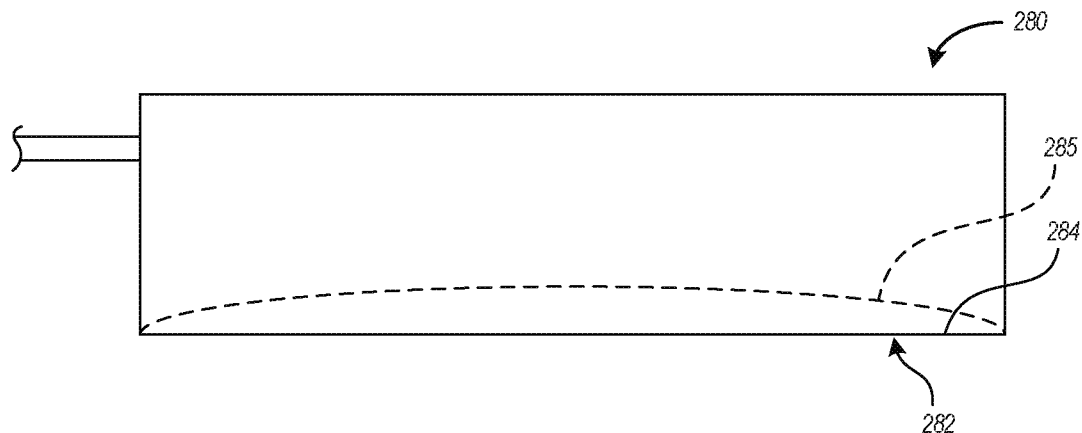

FIGS. 8A to 8C illustrate treatment devices suitable for use with the system 100 of FIGS. 2 and 6 in accordance with embodiments of the technology. FIG. 8A is a schematic, cross-sectional view illustrating an applicator 260 for non-invasively removing heat from target areas of a subject 262. The applicator 260 can include a heat-exchanging unit or cooling device, such as a heat-exchanging plate 264 (shown in phantom line) and an interface layer 265 (shown in phantom line). The interface layer 265 can have a rigid or compliant concave surface 267. When the applicator 260 is held against the subject, the subject's tissue can be pressed against the curved surface 267. One or more vacuum ports can be positioned along the surface 267 to draw the skin 262 against the surface 267. The configuration (e.g., dimensions, curvature, etc.) of the applicator 260 can be selected based on the treatment site.

FIG. 8B is a schematic, cross-sectional view illustrating an applicator 270 that can include a heat-exchanging unit 274 having a rigid or compliant convex surface 276 configured to be applied to concave regions of the subject 272. Advantageously, the convex surface 276 can spread tissue to reduce the distance between the convex surface 276 and targeted tissue under the convex surface 276.

FIG. 8C is a schematic, cross-sectional view illustrating an applicator 280 including a surface 282 movable between a planar configuration 284 and a non-planar configuration 285 (shown in phantom). The surface 282 is capable of conforming to the treatment site to provide a large contact area. In some embodiments, the surface 282 can be sufficiently compliant to conform to highly contoured regions of a subject's face when the applicator 280 is pressed against facial tissue. In other embodiments, the applicator 280 can include actuators or other devices configured to move the surface 282 to a concave configuration, a convex configuration, or the like. The surface 282 can be reconfigured to treat different treatment sites of the same subject or multiple subjects.

Figure 9:
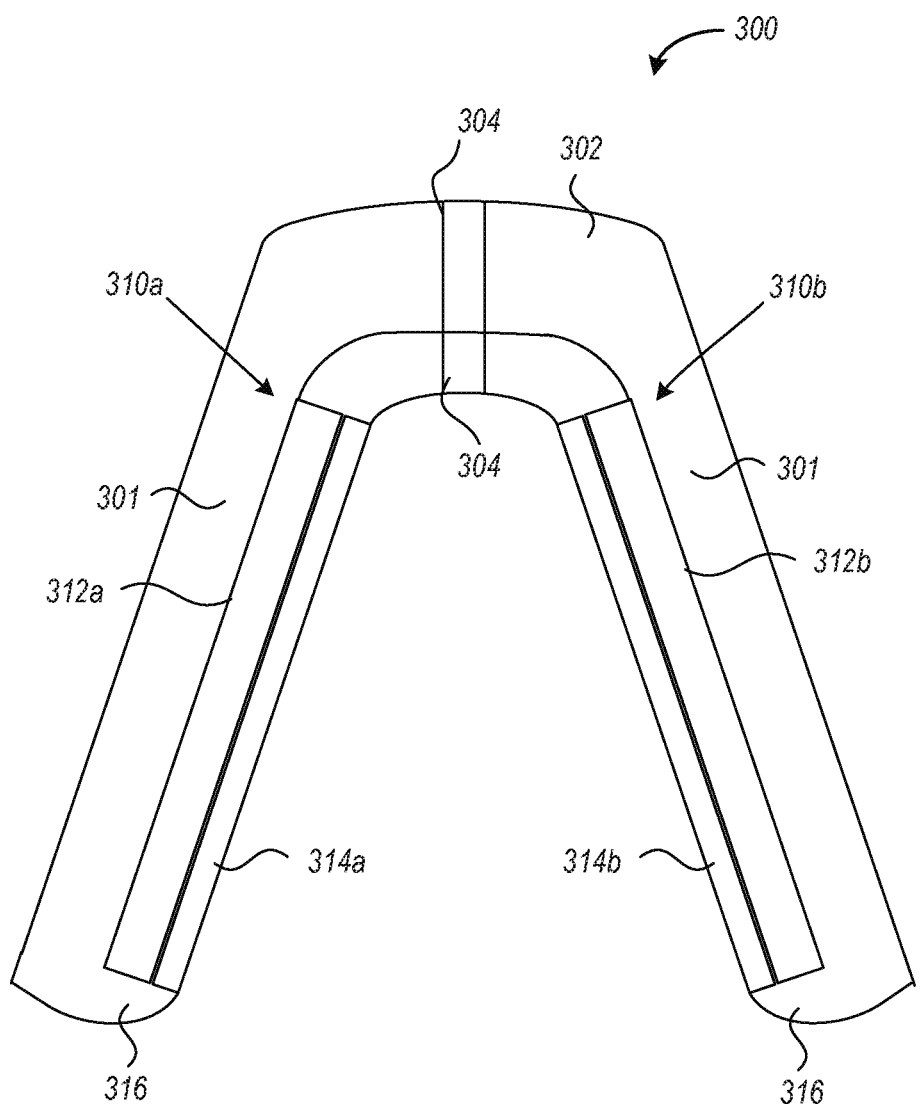
FIG. 9 is a partial cross-sectional view illustrating a vacuum treatment device in accordance with another embodiment of the technology.

FIG. 9 is a schematic, cross-sectional view of an applicator 300 for non-invasively removing heat from target areas in accordance with another embodiment of the technology. The applicator 300 includes a housing 301 having a vacuum cup 302 with a vacuum port 304 disposed in the vacuum cup 302. The housing 301 is coupled to or otherwise supports a first applicator unit 310a on one side of the cup 302, and a second applicator unit 310b on an opposing side of the cup 302. Each of the first and second applicator units 310a, 310b can include a heat-exchanging unit (e.g., a cooling unit, heating/cooling device, etc.) with a heat-exchanging plate 312 (shown individually as 312a and 312b), and an interface layer 314 (shown individually as 314a and 314b). In one embodiment, the heat-exchanging plate 312 is associated with one or more Peltier-type TEC elements supplied with coolant and power from the treatment tower 102 (FIGS. 2 and 6). As such, the heat-exchanging plates 312a, 312b can be similar to the heat-exchanging plate 210 described above with reference to FIG. 7.

The interface layers 314a and 314b are adjacent to the heat-exchanging plates 312a and 312b, respectively. Similar to the interface layer 220 illustrated in FIG. 7, the interface layers 314a and 314b can be plates, films, a covering, a sleeve, a reservoir or other suitable element located between the heat-exchanging plates 312a and 312b and the skin (not shown) of a subject. In one embodiment, the interface layers 314a and 314b can serve as patient protection devices and can include communication components (not shown) and sensors (not shown) similar to those described with respect to the interface layer 220 of FIG. 7 for communicating with the controller 114. In other embodiments, the interface layers 314 can be eliminated.

In operation, a rim 316 of the vacuum cup 302 is placed against the skin of a subject and a vacuum is drawn within the cup 302. The vacuum pulls the tissue of the subject into the cup 302 and coapts the target area with the interface layers 314a and 314b of the corresponding first and second applicator units 310a, 310b. One suitable vacuum cup 302 with cooling units is described in U.S. Pat. No. 7,367,341. The vacuum can stretch or otherwise mechanically challenge skin. Applying the applicator 300 with pressure or with a vacuum type force to the subject's skin or pressing against the skin can be advantageous to achieve efficient treatment. The vacuum can be used to damage (e.g., via mechanically massage) and/or stretch connective tissue, thereby lengthen the connective tissue. In general, the subject has an internal body temperature of about 37° C., and the blood circulation is one mechanism for maintaining a constant body temperature. As a result, blood flow through the skin and subcutaneous layer of the region to be treated can be viewed as a heat source that counteracts the cooling of the desired targeted tissue. As such, cooling the tissue of interest requires not only removing the heat from such tissue but also that of the blood circulating through this tissue. Temporarily reducing or eliminating blood flow through the treatment region, by means such as, e.g., applying the applicator with pressure, can improve the efficiency of tissue cooling and avoid excessive heat loss through the dermis and epidermis. Additionally, a vacuum can pull skin away from the body which can assist in cooling targeted tissue.

The units 310a and 310b can be in communication with a controller (e.g., the controller 114 of FIGS. 2 and 6), and a supply such that the heat-exchanging plates 312a, 312b can provide cooling or energy to the target region based on a predetermined or real-time determined treatment protocol. For example, the heat-exchanging plates 312a, 312b can first be cooled to cool the adjacent tissue of the target region to a temperature below 37° C. (e.g., to a temperature in the range of between about −40° C. to about 20° C.). The heat-exchanging plates 312a, 312b can be cooled using Peltier devices, cooling channels (e.g., channels through which a chilled fluid flows), cryogenic fluids, or other similar cooling techniques. In one embodiment, the heat-exchanging plates 312a, 312b are cooled to a desired treatment temperature (e.g., −40° C., −30° C., −25° C., −20° C., −18° C., −15° C., −10° C., −5° C., 0° C., or 5° C.). In this example, the lipid-rich cells can be maintained at a sufficiently low temperature to be damaged or destroyed.

E. Suitable Computing Environments

Figure 10:
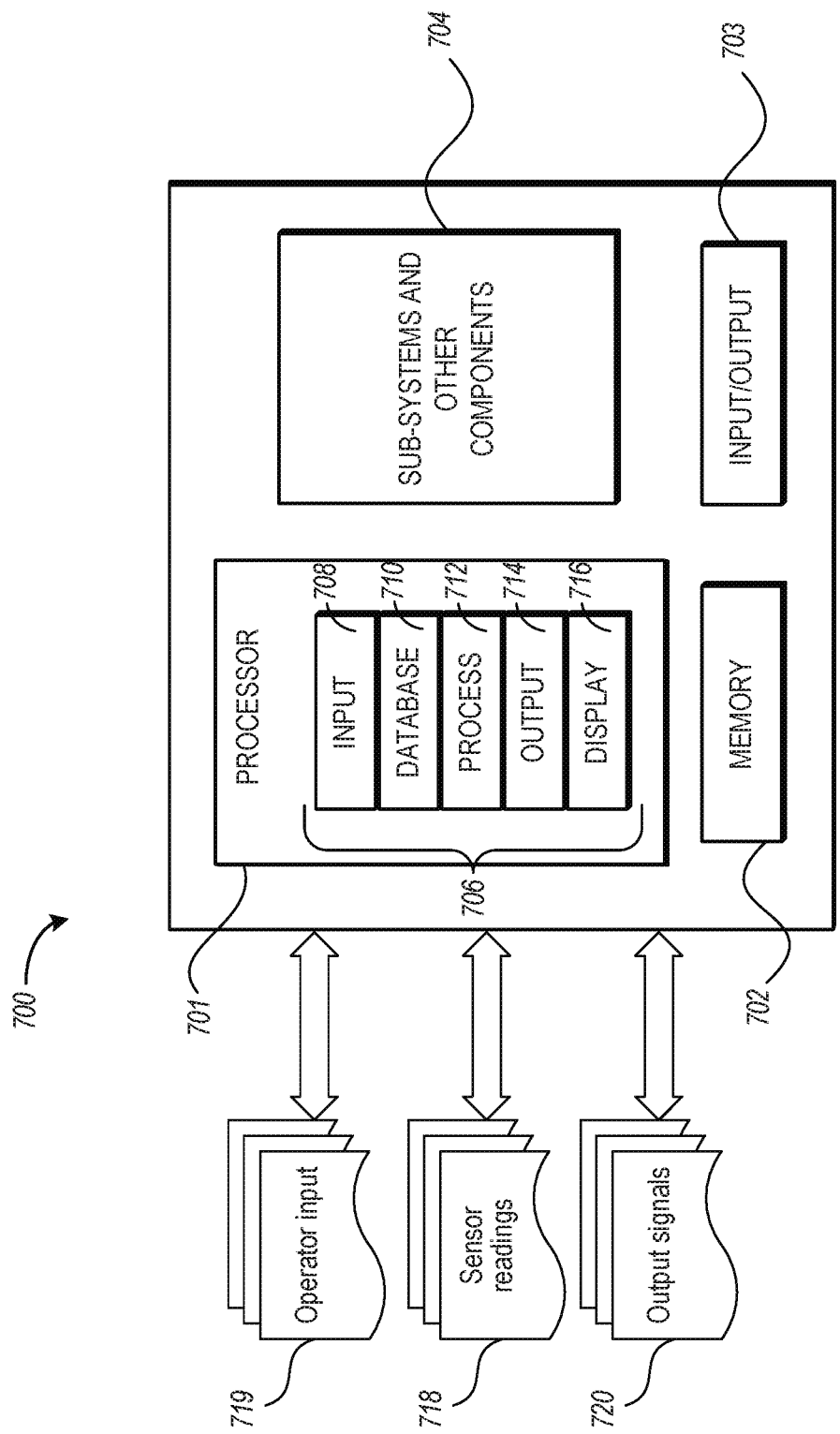
FIG. 10 is a schematic block diagram illustrating computing system software modules and subcomponents of a computing device suitable to be used in treatment systems in accordance with an embodiment of the technology.

FIG. 10 is a schematic block diagram illustrating subcomponents of a computing device 700 suitable for the system 100 of FIGS. 2 and 6 in accordance with an embodiment of the disclosure. The computing device 700 can include a processor 701, a memory 702 (e.g., SRAM, DRAM, flash, or other memory devices), input/output devices 703, and/or subsystems and other components 704. The computing device 700 can perform any of a wide variety of computing processing, storage, sensing, imaging, and/or other functions. Components of the computing device 700 may be housed in a single unit or distributed over multiple, interconnected units (e.g., through a communications network). The components of the computing device 700 can accordingly include local and/or remote memory storage devices and any of a wide variety of computer-readable media. In some embodiments, the input/output device 703 can be the input/output device 120 of FIG. 6.

As illustrated in FIG. 10, the processor 701 can include a plurality of functional modules 706, such as software modules, for execution by the processor 701. The various implementations of source code (i.e., in a conventional programming language) can be stored on a computer-readable storage medium or can be embodied on a transmission medium in a carrier wave. The modules 706 of the processor can include an input module 708, a database module 710, a process module 712, an output module 714, and, optionally, a display module 716.

In operation, the input module 708 accepts an operator input 719 via the one or more input/output devices described above with respect to FIG. 6, and communicates the accepted information or selections to other components for further processing. The database module 710 organizes records, including patient records, treatment data sets, treatment profiles and operating records and other operator activities, and facilitates storing and retrieving of these records to and from a data storage device (e.g., internal memory 702, an external database, etc.). Any type of database organization can be utilized, including a flat file system, hierarchical database, relational database, distributed database, etc.

In the illustrated example, the process module 712 can generate control variables based on sensor readings 718 from sensors (e.g., sensor 167 of FIG. 1B, the temperature measurement components 217 and 227 of FIG. 6, etc.) and/or other data sources, and the output module 714 can communicate operator input to external computing devices and control variables to the controller 114 (FIGS. 2 and 6). The display module 816 can be configured to convert and transmit processing parameters, sensor readings 818, output signals 720, input data, treatment profiles and prescribed operational parameters through one or more connected display devices, such as a display screen, printer, speaker system, etc. A suitable display module 716 may include a video driver that enables the controller 114 to display the sensor readings 718 or other status of treatment progression on the input/output device 120 (FIG. 6).

In various embodiments, the processor 701 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 702 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

F. Conclusion

It will be appreciated that some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. The technology disclosed herein can be used to perform the procedures disclosed in U.S. Provisional Application Ser. Nos. 61/943,257 and 61/943,251, both filed Feb. 21, 2014, U.S.

Pat. No. 7,367,341 entitled "METHODS AND DEVICES FOR SELECTIVE DISRUPTION OF FATTY TISSUE BY CONTROLLED COOLING" to Anderson et al., and U.S. Patent Publication No. US 2005/0251120 entitled "METHODS AND DEVICES FOR DETECTION AND CONTROL OF SELECTIVE DISRUPTION OF FATTY TISSUE BY CONTROLLED COOLING" to Anderson et al., the disclosures of which are incorporated herein by reference in their entireties. The technology disclosed herein can target tissue for tightening the skin, improving skin tone or texture, eliminating or reducing wrinkles, increasing skin smoothness as disclosed in U.S. Provisional Application Ser. No. 61/943,250.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. In those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. While the above description details certain embodiments and describes the best mode contemplated, no matter how detailed, various changes can be made. Implementation details may vary considerably, while still being encompassed by the technology disclosed herein. The various aspects and embodiments disclosed herein are for purposes of illustration and are not intended to be limiting, with the true scope and spirit being indicated by the following claims.

What is claimed is:

1. A method for improving the appearance of skin, the method comprising:

cooling a surface of a patient's skin to a temperature no lower than about −40 degrees C. using a cooling device; and controlling the cooling device to continue to cool the patient's skin for a period of time such that subcutaneous adipose tissue directy below the cooled patient's skin is not injured and such that dermal tissue of the skin is injured, via a cold -induced injury, to improve the appearance of the skin by tightening the skin, improving skin tone or texture, eliminating or reducing wrinkles, increasing skin smoothness, and/or improving the appearance of cellulite, and wherein the period of time being less than about 40 minutes, wherein the cooling device is controlled so that a most significant tissue injury cooling zone in the skin is centered between about 0.5 mm to about 2 mm deep.

2. The method of claim 1, wherein the improvement in the appearance of skin does not include significant lightening or darkening of a color of the skin one or more days after a freeze event, which causes the dermal tissue to be injured, ends.

3. The method of claim 1, further comprising applying sufficient cryoprotectant to the skin to protect epidermal tissue from freeze injury from the cooling device.

4. The method of claim 1, further comprising supplying heat to the subcutaneous adipose tissue transcutaneously through the patient's skin.

5. The method of claim 1, further comprising
cooling the skin sufficiently to cause a freezing event;
detecting the freezing event in the patient's skin; and
controlling the cooling device so that the freeze event lasts for no longer than a second period of time which is longer than about 10 seconds and shorter than 10 minutes.

6. The method of claim 1, wherein the cooling device is controlled to cause skin tightening.

7. The method of claim 1, wherein the cooling device is controlled to at least partially freeze tissue in the most significant tissue injury cooling zone which is within the dermal tissue.

8. The method of claim 1, wherein the skin is facial skin.

9. The method of claim 1, wherein the period of time is shorter than about 30 minutes.

10. A method for improving an appearance of skin, the method comprising: applying a cooling surface of a device to a surface of a patient's skin; and cooling the surface of the patient's skin to a temperature higher than about −40 degrees C. using the cooling surface to keep dermal tissue of the patient's skin within a cold injury temperature range for less than about 40 minutes and long enough to cause a cold injury in the dermal tissue of the patient's skin sufficient to produce the improved appearance of the skin by at least one of tightening the skin, improving skin tone or texture, eliminating or reducing wrinkles, increasing skin smoothness, or improving the appearance of cellulite, wherein the cold injury is centered between about 0.5 mm to about 2 mm deep so as to inhibit injury of subcutaneous adipose tissue directly below the cold injury.

11. The method of claim 10, wherein the cold injury temperature range is below 0 degrees C.

12. The method of claim 10, wherein the improved appearance of the skin is caused by the cold injury to the dermal tissue.

13. A method for altering a patient's skin, the method comprising: applying a cooling surface of a device to a surface of the patient's skin; and cooling the surface of the patient's skin to a temperature higher than about −40 degrees C. using the cooling surface to keep dermal tissue of the patient's skin within a cold injury temperature range for less than about 40 minutes but sufficiently long to cause a cold injury, which is centered at a depth of about 0.5 mm to about 2 mm, in the dermal tissue of the patient's skin, thereby inhibiting injury of subcutaneous adipose tissue directly below the cooled surface and causing an alteration to the appearance of the patient's skin by at least one of tightening the skin, improving skin tone and/or texture, eliminating or reducing wrinkles, increasing skin smoothness, or reducing the appearance of cellulite.

* * * * *